US005858745A

United States Patent [19]

Jellis et al.

[11] Patent Number: 5,858,745

[45] Date of Patent: Jan. 12, 1999

[54] ***BACILLUS THURINGIENSIS* TRANSFORMATION METHOD**

[75] Inventors: Cindy Lou Jellis, Londonberry, N.H.; Noah D. Beerman, Cambridge, Mass.; Jean-Christophe Piot, Menlo Park, Calif.

[73] Assignee: Novartis Finance Corporation, New York, N.Y.

[21] Appl. No.: 957,488

[22] Filed: Oct. 24, 1997

Related U.S. Application Data

[63] Continuation of Ser. No. 770,077, Dec. 19, 1996, abandoned, which is a continuation of Ser. No. 342,938, Nov. 22, 1994, abandoned, which is a continuation of Ser. No. 201,754, Feb. 25, 1994, abandoned, which is a continuation of Ser. No. 63,194, May 17, 1993, abandoned, which is a continuation of Ser. No. 803,248, Dec. 5, 1991, abandoned, which is a division of Ser. No. 570,663, Aug. 22, 1990, abandoned, which is a continuation-in-part of Ser. No. 452,526, Dec. 18, 1989, abandoned.

[51] Int. Cl.[6] ............................ C12N 15/00; C12N 13/00

[52] U.S. Cl. .................................... 435/172.3; 435/173.1; 435/173.3; 435/173.6

[58] Field of Search ............................... 435/69.1, 172.1, 435/172.3, 172.6

*Primary Examiner*—James Ketter
*Assistant Examiner*—Irem Yucel
*Attorney, Agent, or Firm*—Larry W. Stults, Ph.D.

[57] ABSTRACT

Particularly effective *B.t.* insecticides are obtained by culturing to the sporulation stage novel transformant obtained on transforming *B.t. kurstaki* H.D. 562 with DNA expressing in the *B.t.* certain mutant endotoxin genes. Such transformants and other *B.t.* transformants generally may be obtained in high transformation frequencies by the electrotransformation of *B.t.* cells while in a hypertonic state followed by maintaining the cells in a hypertonic medium for a time sufficient to obtain intact cells. Transformation of *B.t. tenebroinis* and *B.t. aizawai* is also described.

20 Claims, 6 Drawing Sheets

Sma I   Sca I        Mlu I

Chlor                DET pBEV210TL ori        Pro.
                     Spe I

KEY

■  TRANSCRIPTION TERMINATION LOOP

↗  E. coli/B.t. TANDEM PROMOTERS

Chlor  CHLORAMPHENICOL RESISTANCE

DET    B.t. wuh. DELTA-ENDOTOXIN GENE ori    E. coli ORIGIN OF DNA REPLICATION

*BACILLUS THURINGIENSIS* TRANSFORMATION METHOD

This is a Continuation of application Ser. No. 08/770,077, filed Dec. 19, 1996, now abandoned, which is a Continuation of application Ser. No. 08/342,938, filed Nov. 22, 1994, now abandoned, which is a Continuation of application Ser. No. 08/201,754, filed Feb. 25, 1994, now abandoned, which is a Continuation of application Ser. No. 08/063,194, filed May 17, 1993, now abandoned, which is a Continuation application Ser. No. 07/803,248, filed Dec. 5, 1991, now abandoned, which is a division of application Ser. No. 07/570,663, filed Aug. 22, 1990, now abandoned, which is a continuation-in-part of application Ser. No. 07/452,526, filed Dec. 18,1989, now abandoned.

Delta-endotoxin proteins, produced by the sporulating bacterium *Bacillus thuringiensis* (*B.t.*) as protein crystals at the end of its vegetative growth, are a potent insecticide against specific insects. The genes responsible for the production of the endotoxin are found on one or more plasmids within the natural *B.t.* cell. Certain of these plasmids have been isolated, the endotoxin producing genes located and excised, the genes sequenced and the amino acid sequence (structure) of the endotoxins deduced. The precise amino acid structure of the toxic portion of certain endotoxins produced by the wild type organisms is therefore also known, and it has been determined that the endotoxin is a precursor molecule which, it is generally believed, is cleaved by proteases in the insect gut to release the toxic portion. Truncated molecules, ie. those shorter than the full length endotoxin, have been demonstrated to be active. Pending U.S. patent application Ser. No. 07/160,233, filed Feb. 25, 1988, which has published foreign counterparts, eg. in British Application No. 2216127 (published Oct. 4, 1989), the disclosure of which is incorporated herein by reference, describes full length and truncated endotoxin molecules which are mutated in the active toxin portion and which are indicated to have up to five times increased toxicity.

In our prior application Ser. No. 452,526, filed Dec. 18, 1989, we described a number of inventions including novel vectors, an improved electrotransformation process for *B.t.* cells, DNA conditioning for transforming certain *B.t.* species and various new *B.t.* transformants harboring or transformed with native or mutant endotoxin genes.

BRIEF SUMMARY

The present invention concerns particularly active *B.t. kurstaki* insecticides provided when certain *B.t. kurstaki* cells are transformed with DNA carrying an expressible gene encoding certain mutant *B.t.* endotoxins described in said U.S. application Ser. No. 07/160,233 herein also "prior application".

More particularly, new *B.t.* type insecticides having potent and desirably insecticide activity are provided when an expressible exogenous gene encoding an endotoxin having one or more of the mutations described as p26-3 and p98c1 in said prior application are transformed into and harbored by the known *B.t. kurstaki* strain type H.D. 562.

The present invention also concerns the improved process for the electrotransformation of *B.t.* cells in which the cells are transformed in a hypertonic state and maintained in a hypertonic aqueous media following transformation for a time to sufficient to obtain intact cells. High transformation efficiencies are obtained.

*B.t. Tenebrionis* and *B.t. aizawai* may also be transformed and the resulting transformants and other subject matter which currently remains claimed in the parent application are also disclosed.

DESCRIPTION OF THE DRAWINGS

The present invention will be more particularly evident from the following description and accompanying drawings in which.

Figure 1:
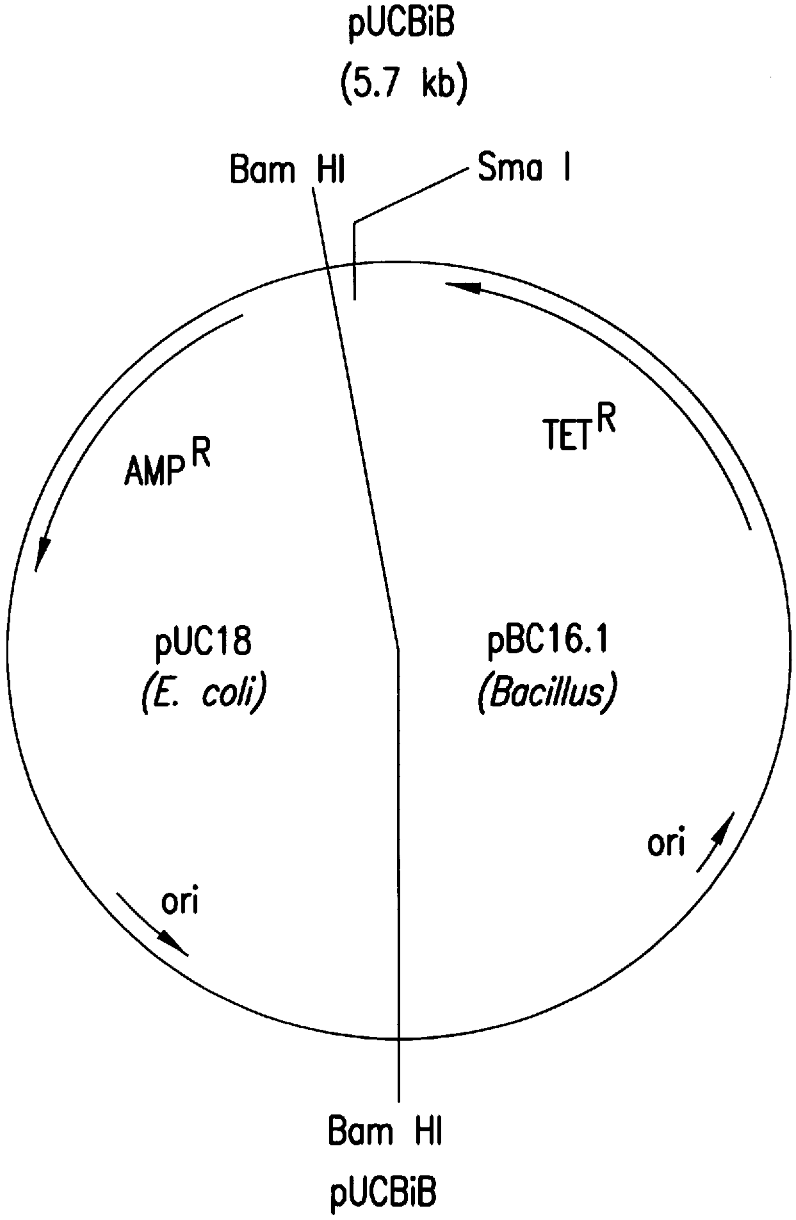
FIG. 1: illustrates the shuttle plasmid or vector pUC:BiB produced from plasmids pUC18 and pBC16.1.

The vector pK8-1 herein has been deposited NRRL B-15967 on Apr. 24, 1985 and the vector pBT210 has been deposited NRRL B-18330 on Feb. 19, 1988, both of which deposits shall be made available for this application.

DETAILED DESCRIPTION

As disclosed in said U.S. application, Ser. No. 07/160,233 and its foreign counterparts, there are a number of mutations or amino acid changes which can be made in a *B.t.* endotoxin, whereby enhanced activity was indicated. Table A hereto (which is also given and described in said prior applications) gives the full length DNA and amino acid sequences of a *B.t.* endotoxin of *B.t. wuhanensis* and, as recognized in the art, the encoded amino acid sequence for the active portion of the protein and beyond, in particular from the N-terminus up to at least the indicated Kpn I site in the protoxin portion, is the same as found in other *B.t.* species and varieties, in particular *B.t. Kurstaki* HD-1. Differences beyond the Kpn I site are also relatively few. Hence, the sequence given in Table A fairly represents a common endotoxin sequence, particularly in its active portion, and has, particularly as regards the active portion, a high degree of homology or similarly to other *B.t.* endotoxin. Table A numbers the amino acid of the full sequence 1 to 1181 in parenthesis below the amino acid. Nucleotides in the structured gene are numbered (not in parenthesis) above the line in which they appear and the last digit in the number stands above the nucleotide to which the number applies. Within the numbered sequences indicted above a portion thereof is separately or sub-numbered m-1 through m-116 for amino acids and n-1 through n-348 for the nucleotides for such amino acids, to more particularly indicate a highly conserved region in which certain of mutations described in said prior applications are located. Certain restriction sites relevant to the nucleotide sequence are shown by a line above the nucleotides involved in the restriction sites with a footnote designation of the particular site. The toxic portion of the endotoxin shown in Table A as recognized in the art involves the amino acid sequence beginning at amino acid position 1 (Met) and extending through amino acid position 610 (Thr).

As indicated from the results in Example 7, mutations from two of those previously described and designated "26-3" and "98c1" in said prior applications were indicated to have unexpectedly beneficial influence on insectical activity when transformed into the known endotoxin-producing *B.t. Kurstaki* strain H.D. 562. These involved mutations, as described in the prior application are as follows:

| | Position No. | "m" Position | Change In Endotoxin Area | |
|---|---|---|---|---|
| Mutant | Full Length | Number | Nucleic Acid | Amino Acid |
| p 26-3 | 119 | m-30 | GCA → ACA | Ala → Thr |
| | 130 | m-41 | ATG → ATA | Met → Ile |
| | 201 | m-112 | GGC → GAC | Gly → Asp |
| p 98cl | 188 | m-99 | ACT → TCT | Thr → Ser |

Hence, by present invention there may also be produced particularly effective insecticids of the *B.t.* type by growing to the sporulation stage at which endotoxins are expressed or produced cells of a *Bacillus thuringiensis Kurstaki* strain H.D. 562 which comprises or harbors its native plasmids for expression of its native *B.t.* endotoxins and also harbors or is transformed with heterologous DNA comprising an orgin of replication in said *B.t.* cells and DNA encoding a *B.t.* operable gene for the expression of a mutant *B.t.* endotoxin protein having insecticidal activity against tobacco budworn larva upon ingestion by the insect, the structural gene DNA for said mutant protein characterized by having a DNA portion coding for an amino acid sequence having substantial amino acid homology with the 116 amino acid sequence encoded by the DNA beginning at position m-1 and extending through postion m-116 in Table A hereof, said position numbers applying to such homologous sequence independent of any deletions or additions therein compared to said 116 amino acid sequence, and said DNA portion being further characterized by any one or more of the following amino acids being coded for by said DNA at the indicated amino acid reference positions: a) at position m-30 any natural amino acid except Ala; b) at position m-41 any natural amino acid except Met; c) at position m-99 any natural amino acid except Thr; and d) at position m-112 any natural amino acid except Gly.

The indicated point mutations may be applied to endotoxin protein sequences produced by *Bacillus thuringiensis* varieties and subtypes, which sequences are insecticidal active against Lepidopteran larvae as indicated by the Tobacco Budworm Assay herein described when containing the indicated 116 amino acid conserved sequence or a sequence which is highly homologous therewith or essentially an equivalent thereof, including preferably protein endotoxin sequences which are of the natural full length type or substantially full length, but also those which are truncated by removal of all or a part of downstream protoxin or inactive portion thereof (which extends upstream from the endotoxin normal C-terminus to the point of cleavage in the insect gut); and even those which may be truncated from the normal C-terminus upstream and back into the active portion of the endotoxin. Endotoxins from *B.t. Kurstaki* and *B.t. Wuhanensis* have the identical 116 amino acid conserved region and others have or can be expected to have the same 116 amino acid sequence or a largely homologous equivalent thereof. For example, endotoxins from *B.t. Sotto, B.t. Kurstaki* HD-73 (strain), and *B.t. Galleriae* are already also known to produce endotoxins with the idential 116 amino acid sequence even though some of these differ to at least some extent, and in some cases significantly, in both the balance of the toxic portion of the endotoxin and in the protoxin section. Others such as *B.t. Kurstaki* HD-1 Dipel (a commercial substrain) have one amino acid change in the indicated 116 amino acid sequence (m-59 is Leu coded for by TTG) and other changes/deletions/additions in other sequence portions. This and others found to have a single or multiple changes but amino acid homology of at least about 70% to said 116 amino acid sequence may have one or more of the indicated mutant changes made to the amino acids therein which correspond (identically) to the amino acid in said 116 amino acid non-mutated sequence, particularly when the amino acid to be changed has on each of its sides 2 and preferably 4 other amino acids which also correspond (identically) to those in the 116 amino acid sequence. The indicated mutations may be made to corresponding amino acids in homologous series which essentially contain deletions or additions such that the sequence itself is shorter or longer that the indicated 116 amino acid reference sequence. In such cases, each corresponding amino acid in the sequence to be changed will be assigned a position number which is the same as the amino acid to which it is found to correspond (identically) in the indicated 116 amino acd reference sequence, e.g. assigned position number m-5, m-6, etc. In such cases, deletions existing in the sequence to be changed will be counted as actually present and additions in the sequence to be changed will simply not be counted. Hence, amino acid positioning assignment can be said to be made independent of deletions or additions in such a homologous sequence.

Preferably, the homologous amino acid sequences into which the mutant changes may be substituted are those which are coded for by DNA to which DNA from either the sense or antisense strand (or double strand) of the DNA beginning with position n-1 and extending through position n-348 in Table A will hybridize under stringent hybridizing conditions when the homologous sequence to be mutated has its amino acids which correspond to those in the referenced 116 amino acid sequence coded for by the same codon as the corresponding amino acid in the reference sequence. Procedures for preparing such a tagged hybridization probe are well known in the art. Stringent hybridizing conditions are those in which hybridization is effected at 60° C. in 2.5× saline citrate buffer (a.k.a. SSC buffer) followed merely by rinsing at 37° C. at reduced buffer concentration which will not affect the hybridizations which take place.

More preferably, the mutations are made in amino acid sequences which have no more than 1, 2 or 3 amino acid differences from those in the 116 amino acid reference sequence, most preferably a sequence which is identical to the reference sequence.

It is already clearly indicated in the art that the 116 amino acid reference sequence may form a portion of otherwise substantially modified or different endotoxin protein sequences which have insecticidal activity against Lepidopteran larvae, and other modifications outside of the reference sequence and perhaps even within the reference sequence will most certainly be uncovered as knowledge of the art unfolds. Hence, the sequences bordering the required mutated sequence portion which is analogous to the 116 amino acid reference portion may vary to a considerable extent and need only be sufficient to provide insecticidally active endotoxin protein (eg. insectically active against the Tobacco Budworm). Thus, the amino acid sequence upstream from the mutated portion may be shortened or lengthened or itself mutated relative to the sequence shown in Table A, but will generally begin with methionine and is most preferably highly homologous (70%) or identical to that shown in Table A. Similarly, the portion downstream from the required mutated sequence portion may vary widely and be shortened or lengthened relative to the balance thereof shown in Table A up to its point of cleavage in the insect gut, and of course may or may not be further extended to form a protoxin or inactive portion subject to cleavage in the insect gut to provide an insecticidally proitein toxin. It is judged usually preferred to employ or produce fuller length sequences which are the same as or mimick the native type at least in terms of the opportunity to achieve an endotoxin protein folding capablity similar to that of its native capability, or an improved full length folding effect. Preferably, the fuller length sequence into which the mutations are made will have at least 70% amino acid homology to the amino acid sequence 1 to 1181 in Table A or the double stranded DNA shown in Table A as encoding said 1 to 1181 amino acid protein will hybridize under stringent conditions to the fuller length mutated sequence. More preferably, the mutated DNA will code otherwise for the 1181 amino acid protein in Table A, or for a functional equivalent of the mutant protein which substantially provides the advantages thereof in H.D. 562.

In general, for purposes of this application, the DNA to be mutated will code for an endotoxin having activity against the tobacco budworm as would be recognized in the art or when not so apparent may be determined by assay using, for example, the non-mutant gene transformed into Cry B and assaying for activity compared to the essentially inactive untransformed Cry B in a standard budworm assay as described in Example 7, hereof. While such activity will be indicated when providing an $LD_{25}$ at the highest 10% culture concentration, the preferred substrates for mutation will have at least about the budworm activity provided by the vector pBT1000 (herein described) when transformed into Cry B.

Preferably, the mutant amino acid at m-30 is Thr, at m-41 is Ile, at m-99 is Ser and at m-112 is Asp.

As regards the three mutations in the mutated sequence p26-3, one or two of these may be omitted but preferably all three will be used together.

*B.t. Kurstaki* is well-known and exists in several varieties or strains, the taxonomic distinctions among which are established. Mutants strains which are essentially substrains are also known. The *B.t. kurstaki* strain H.D. 562 is well-known and publically available from the National Regional Research Laboratory at Peoria, Ill. U.S.A., under the Accession No. NRRL H.D. 562. Desirably, the mutant-containing DNA is transformed into cells of the well known *B.t. Kurstaki* H.D. 562 substrain which is represented by the commercial substrain JAVELIN®. Spores for growth and transformation of such preferred substrain may be obtained from the commercial product.

The *B.t. Kurstaki* cells transformed with or harboring the mutated endotoxin genes as above identified are stable when maintained in the presence of anti-biotic against which the cells express resistance, eg. tetracycline for which resistance is expressed by the plasmid carrying the mutant endotoxin gene. The cells produce at sporulation a biomass which comprises spores of the *B.t.* along with the native endotoxins produced by the untransformed cells and the mutant endotoxin protein encoded by the DNA inserted on transformation. Such spore-containing biomass and concentrates thereof can be understood as broadly comprising a mixture of the expressed endotoxins which is new and in which the endotoxins are indicated to associate to provide particularly desirably insectical activity by way of level and spectrum of activity, and in particular substantial enhancement of activity against Spodoptera.

The new *B.t. kurstaki* transformants may be prepared employing certain plasmids and electrotransformation procedures herein described.

Plasmids

Plasmid vectors, which may be used to transform two taxonomically different bacterial hosts, wherein said first host is *E. coli* and said second host is the Bacillus species, comprise:

i) a region of DNA enabling replication of the vector in a first bacterial host, ii) a region of DNA enabling replication of the vector in a second bacterial host, iii) means for selecting transformed first and second hosts, iv) a region of DNA enabling gene expression in a first bacterial host, v) a region of DNA enabling gene expression in a second bacterial host, vi) a DNA sequence which upon expression encodes a *B.t.* DET.

In one embodiment of such a plasmid, efficient means are provided for deleting a sequence of DNA from the plasmid, such sequence containing the sequence enabling replication in the first host, prior to the transformation of the Bacillus host if such sequences are undesirable.

A vector containing an origin of replication operable in *E. coli*, and means for selecting *E. coli* cells transformed with the vector; an origin of replication operable in organisms of the Bacillus species, and means for selecting Bacillus cells transformed or transfected with the plasmid and a DET DNA sequence, in association with both *E. coli* and *B.t.* regulatory sequences, may be used to transform both the *E. coli* and Bacillus hosts, such that the DET sequence may be successfully expressed in both the hosts.

The delta endotoxin sequence for insertion into the plasmid may be a DNA sequence of any of the *B.t.* varieties or subtypes, which, upon expression in both *E. coli* and a cell of the Bacillus species, encodes a delta endotoxin protein. Suitable examples of such are the sequences of the natural full length type or substantially full length, and those which are truncated by removal of all or a part of downstream protoxin or inactive portion thereof (which extends upstream from the endotoxin normal C-terminus to the point of cleavage in the insect gut) and even those which may be truncated from the normal C-terminus upstream and back into the active portion of the endotoxin. Sequences which upon expression encode a fusion protein between, for example, the endotoxin proteins of different *B.t.* strains or DNA sequences into which selective mutations have been engineered to alter the amino acid sequence of the natural endotoxin sequence are also suitable for expression in the plasmid of the invention.

The full length endotoxin structural gene from *Bacillus thuringiensis* var *wuhanensis* (*B.t.w.*) is incorporated, for example, in plasmid pBT210, described in pending U.S. patent application Ser. No. 07/160,233, supra, and publicly available from the Agricultural Research Culture Collection (NRRL), Peoria, Ill. under Repository No. B-18330. This plasmid is a fully competent *E. coli* expression vector and comprises an *E. coli* promoter, a *B.t.* ribosome binding site and a gene for chloramphenicol resistance. The 610 amino acids of the active portion of the encoded *B.t.* endotoxin and extending into the protoxin region (at least up to the KpnI site in encoding DNA in pBT210) is identical to the corresponding sequence of a CryI A(b) type gene cloned from *B.t.* var *kurstaki* (*B.t.k.*) HD-1 (see Hofte & Whitely, Microbiological Reviews, June 1989, Vol. 53, No. 2, pages 242–255 for classification of cells). There is also substantial homology in the balance of the protoxin between pBT210 and *B.t.k.* HD-1.

A truncated endotoxin sequence is contained, for example, in the plasmid prAK, described in pending U.S. patent application Ser. No. 07/160,233, supra, and publicly available from the Agricultural Research Culture Collection (NRRL), Peoria, Ill. under Repository No. B-18329. prAK is a fully competent expression vector for *E. coli* and includes an ampicillin resistance gene, an origin of replication and operator sequences including an *E. coli* promoter. The *E. coli* operator sequence, as found in both pBT210 and prAK, is described in U.S. Pat. No. 4,721,671, and contains a promoter sequence, ribosome binding site (RBS) and a DNA coding sequence, the latter hereinafter being referred to as the *E. coli* gene. It also includes, in proper reading frame co-ordination with the promoter, a DNA sequence which is found in the wild type *B.t.k.* strain HD-1 (a Cry 1 A(b) type gene) (from a portion of the 5.3 kb Hind III class segment as reported, for example, by Kronstad et al., 1983, J. BACTERIOL 154:419–428). The mature sequence has been shortened to code for a truncated *B.t.* endotoxin which includes the entire native toxic portion extending from amino acid position one to amino acid position 610 and further extending into the protoxin portion to end with amino acid position 723. Downstream, or 3', of this it includes a short DNA sequence of 54 bp following the triplet for amino acid 723 and which is itself terminated by a stop signal. This 54 bp sequence originates from the plasmid pBR322. Upstream of the coding sequence and downstream of the *E. coli* gene, prAK contains a sequence which includes a *B.t.* ribosome binding site. The upstream regulatory sequences and the DNA sequence coding for the promoter sequence and the DNA sequence coding for the first 610 amino acids of the active portion of the endotoxin are identical to the *B.t.w.* endotoxin sequence contained in plasmid pBT210, above. Upstream of the coding sequence, the sequence of prAK is virtually identical to that of pBT210, with a few insignificant nucleotide changes, whose presence is due to the different ligation procedures used in the construction of the two plasmids.

The full length endotoxin structural gene from *Bacillus thuringiensis* var. *wuhanensis* (*B.t.w.*) is described in pending U.S. patent application Serial No. 07/160,233, supra, and publicly available from the Agricultural Research Culture Collection (NRRL), Peoria, Ill., under Repository No. B-18330. This plasmid, (pBT210), is a fully competent *E. coli* expression vector and comprises an *E. coli* promoter, a *B.t.* ribosome binding site and a gene for chloramphenicol resistance.

Mutant analogues of both the WT full length structural *B.t.* DET and the WT truncated *B.t.* DET are described in pending U.S. patent application Ser. No. 07/160,233, supra. Any of the mutant sequences described therein, or sequences containing other mutations, may suitably be used in the plasmid of the invention. Hence, full length mutant sequences, such as pBT26-3 and PBT-C are contained in plasmid pBT210, above, and may readily be excised from such plasmids for use in the vector of the invention.

Preferably, the DET DNA sequence is associated with regulatory sequences, which control expression in the two host bacterial cells. The 5' regulatory sequences preferably include a promoter sequence operable in *E. coli* and cells of the Bacillus species. The sequence illustrated below, which is the naturally occurring regulatory sequence of the DET gene, is a particularly suitable *B.t.* operator sequence, containing sites for initiation of RNA synthesis during early (*B.t.* I) and late (*B.t.* II) stages of sporulation, a ribosome binding site (RBS), from which translation of the mRNA initiates, and an initiation codon (Met). [wong, et al., J. Biochem. 1983 258(3):1960–1967]. A *B.t.* sequence, such as that depicted below, is also functional in *E. coli*, resulting in expression of the DET protein in *E. coli* cells at a low level.

```
HpaI                      A & T rich region
GTTAACACCCTGGGTCAAAAATTGATATTTAGTAAAATTAGTTGCACTTTGTGCATTTTT

          B.t. II                B.t. I
TCATAAGATGAGTCATATGTTTTAAATTGTAGTAATGAAAAACAGTATTATATCATAATG

                                   RBS            Met
AATTGGTATCTTAATAAAAGAGATGGAGGTAACTT  ATG . . .
```

Figure 2:
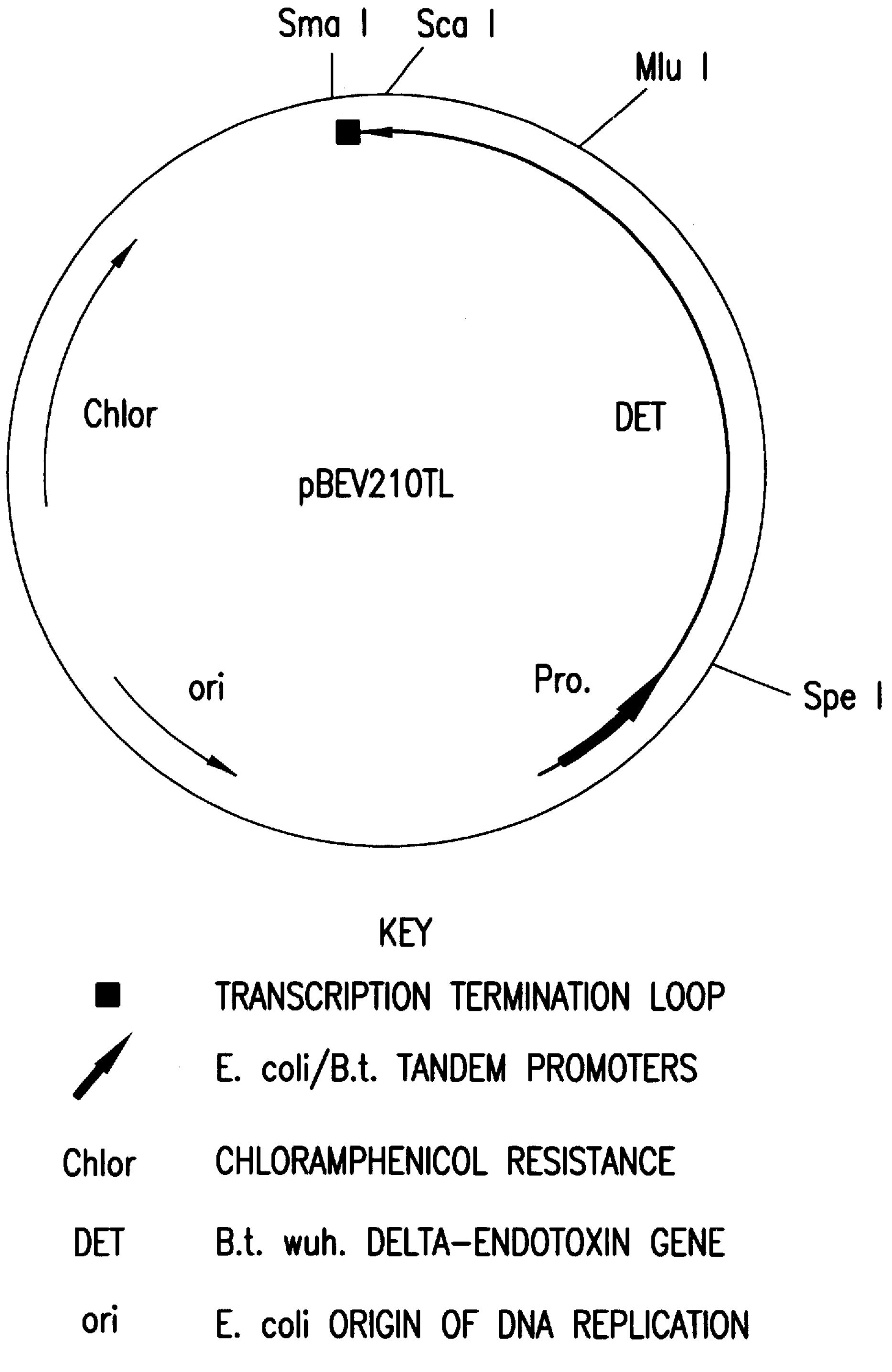
FIG. 2: illustrates the expression vector pBEV210-TL.

A DNA fragment containing the above sequences, as well as coding sequences for the first 450 amino acids of the *Bacillus thuringiensis* var. *kurstaki* strain HD-1 delta endotoxin may be obtained from, for example, the plasmid pK8-1, as described in pending U.S. patent application Ser. No. 06/745,354, filed Jun. 14, 1985, the disclosure of which is incorporated herein by reference, which plasmid is publicly available from the Agricultural Research Culture Collection (NRRL), Peoria, Ill. under Repository No. B-15967. Plasmid pK8-1 is a pBR322 based plasmid containing a portion of the *B.t.k.* DET gene. The DET on expression reacts positively with anti-serum prepared against the 130Kd protoxin and is toxic to *Heliothis virescens* larvae in an insect toxicity assay. The fragment as described above, may be cloned into a plasmid harbouring:a promoter operable in *E. coli* and directing expression of a DET sequence in *E. coli* (c.f. FIG. 2), such as, for example, prAK, described above. Thus, by specific endonuclease digestion, a region of the prAK DNA containing the 5' coding sequences of the DET and the 3' portion of the *E. coli* portion of the *E. coli* gene, may be replaced with the DNA sequence of pK-8-1, described above. The 3' junction formed between the prAK and pK8-1 fragments is within the *B.t.* DET coding sequences and the correct reading frame is maintained by the insertion, such that the toxin gene is exactly as it is found in prAK. By virtue of digesting prAK downstream of the *E. coli* promoter and RBS found therein, i.e. at a site within the *E. coli* gene, and ligating the pK8-1 fragment to this promoter-containing prAK fragment, the prAK-pK8-1 5' junction results in tandem *E. coli*/*B.t.* promoters. Tandem *E. coli*/*B.t.* promoters, as used herein, means the *E. coli* promoter, RBS and the 5' region of the *E. coli* gene, in tandem with the *B.t.* promoter. Translation of the *E. coli* gene results in production of 24 amino acids before this prAK-pK8-1 5' junction is reached. During expression in *E. coli*, translation will start at the ribosome binding site in the *E. coli* promoter and will carry on through the prAK-pK8-1 5' junction into the *B.t.* promoter sequence for a total of 7 amino acids before a stop codon (TGA) is randomly generated. Although the ribosomes will fall off at this stop codon, they recognize the *B.t.* ribosome binding site downstream of this and bind the mRNA, such that, in *E. coli*, the DET is produced as a non-fusion protein with the correct amino terminus shown below, typically at a level of 2–5% of total cellular protein.

NruIHpaI STOP
(E. coli gene) T CGA ACA CCC TGG GTC AAA AAT TGA . . .

. . . (115 bases) . . . AGATGGAGGTAA CTT ATG . . .
B.t. RBS (Start B.t. DET)

The plasmid produced by a ligation such as that described above will thus contain host specific promoters, for *E. coli* and Bacillus species, and also a truncated DET sequence of 723 amino acids, as found originally in prAK.

As described above, the plasmid pBT210 contains the full length structural DET gene, with an associated operator sequence, as in prAK, operable in *E. coli*. To obtain a full length structural DET gene in association with tandem *E. coli/B.t.* promoters, a fragment of pBT210 containing the *E. coli* RBS, and 5' portion of the *E. coli* gene and the sequence coding for the first 450 amino acids of the B.t. DET may be excised and replaced with a fragment from a plasmid, such as that produced by the ligations described above, containing the tandem *E. coli/B.t.* promoter sequences and a region encoding the identical 450 amino acids of the DET protein. In this manner the correct reading frame for the DET will be retained and the resulting plasmid will express the full length structural DET in *E. coli*.

Described in more detail in the Examples, a specific example of the above process can be summarized as follows: plasmid prAK is digested with NruI and SstI. The NruI site, at position 575, is within the *E. coli* gene sequence, downstream of the *E. coli* promoter and RBS, and the SstI site is within the DET coding sequence. The larger fragment (3.9 kb) is isolated. Plasmid pK8-1 is digested with HpaI and SstI. The HpaI site is at the 5' end of the *B.t.* promoter and the SstI site is within the DET coding sequence, this site being identically positioned with that in prAK. The 1.5 kb fragment thus produced is isolated and ligated with the 3.9 kb prAK fragment. The blunt end digestion/ligation at the NruI and HpaI sites causes destruction of these two sites. The resulting hybrid plasmid, pBEV100, containing the *E. coli* operator portion from prAK and C-terminal DET sequence, *B.t.* promoter and N-terminal DET sequence of pK8-1, is digested with HpaI and SstI. The HpaI site is located downstream of the *E. coli* promoter, between this and the RBS, at position 448. Plasmid pBT210 is likewise digested with HpaI and SstI, the HpaI site (at position 448) again lying between the *E. coli* promoter and the RBS, and the larger, 6.9 kb, fragment of pBT210 ligated with the smaller, 1.6 kb, fragment of pBEV100. The resulting plasmid, pBEV210, contains the *E. coli* operator and *B.t.* promoter exactly as in pBEV100, in association with the full length structural DET gene sequence. The ligation at HpaI and SstI restores these sites.

Further regulatory sequences which are preferably associated with the DET coding sequence include the 3' transcription termination loop (Wobiko, et al., 1986 DNA 5:305–314). This regulatory element, consisting of a sequence of dyad symmetry, is found in naturally occurring *B.t.* DET genes after the coding portion of the gene and is thought to lead to increased mRNA stability. Complementary oligonucleotides which code for this regulatory element may be cloned downstream, or 3', of the DET coding sequence. For example, with plasmid pBEV210, the production of which is described above, a partial digestion with PvuI creates a linear DNA molecule, the PvuI site, at position 4444, being immediately downstream of the full length structural DET gene sequence contained in pBEV210. Complementary oligonucleotides coding for the 3' transcription termination signal, with PvuI sticky ends may be ligated into this PvuI digested pBEV210, thereby inserting the 3' signal and forming plasmid pBEV210-TL. With the correct orientation of the oligonucleotides, the SmaI site found therein, will be situated at position 4490, immediately upstream of the 3' PvuI ligation site.

The DNA sequences which permit a plasmid to act as an autonomous replicon in its host cell include the origin of replication. Such sequences are host specific, in that a sequence which will allow a plasmid to replicate in a bacterium of one genus will typically not enable replication of that plasmid in a bacterium of a different genus. Many plasmids which are capable of self-replication in *E. coli* and which may be used in the formation of the plasmid of the invention, are known in the art, for example pBR322, pUC, pK and derivatives thereof. (Plasmids pK18 and pK19 are described, for example, in Pridmore 1987 Gene 56:309–312). In the construction of the plasmid of the invention, it is preferred that sequences derived from the pUC derivatives pUC18 or pUC19 (Bethesda Research Labs) are employed, and more preferably pUC18. pUC18 is a cloning vector with a total size of approximately 2.7 kb and contains a gene conferring ampicillin (amp) resistance on a host transformed with the plasmid. It further contains a unique EcoR1 restriction endonuclease recognition site.

An example of a plasmid which replicates in *Bacillus sp.* is pBC16.1, described by Perkins and Youngman, 1983 J. Biochem. 155(2):607–615. This plasmid originates from a German isolate of *B. cereus* and has a total size of approximately 2.9 kb. The plasmid also carries a gene encoding tetracycline (tet) resistance. There is a unique EcoR1 restriction endonuclease recognition site into which may be cloned DNA sequences of interest.

By a simple digestion and ligation procedure, utilizing a restriction site unique to both vectors, plasmids pUC18 and pBC16.1, for example, may be combined, such that the resulting clone contains origins of replication permitting autonomous replication in both *E. coli* and Bacillus species, an amp resistance gene and a tet resistance gene for selection of transformed hosts.

The shuttle vector pUC:B is produced from the ligation of pUC18 and pBC16.1. One of the EcoR1 sites at the junction of these two original plasmids can be changed to, for example, a BamHI site (c.f. FIG. 1 and Example 1). This step is done prior to cloning in the DET gene sequences. The resulting plasmid is referred to as pUC:BiB and shown in FIG. 1.

For expression of DET genes in *E. coli* and *Bacillus sp.*, the DET DNA is cloned into pUC:BiB. Preferably the DET DNA sequence will consist of the full length structural gene in association with 5' and 3' regulatory sequences, including the *B.t.* promoter and 3' transcription termination to make pBEV210TL as shown in FIG. 2.

The DET coding and regulatory sequences contained in pBEV210-TL, described above, are preferably cloned into a restriction endonuclease site within the multiple cloning site, upstream of the BamHl site of the shuttle vector pUC:BiB. A suitable site for such insertion is the Smal site. The resulting plasmid, termed pBt1000, is thus formed by excising a Hpal-Smal fragment from pBEV210-TL and inserting this into the Smal site of pUC:BiB. The Hpal digestion occurs at position 448 of pBEV210-TL, and is thus at the site used in the formation of pBEV210-TL. Therefore, the Hpal-Smal fragment inserted into the pUC:BiB vector contains the RBS from the *E. coli* operator, 5' portion of the *E. coli* gene, *B.t.* promoter and the sequence encoding the full length structural DET protein, up to and including the 3' transcription termination signal. pBt1000 thus contains the above sequences, an origin of replication for *E. coli* and means for selection of transformed *E. coli* hosts, and an origin of replication for Bacillus cells with means for selection of transformed Bacillus hosts. This plasmid may be used to amplify the total DNA in *E. coli* and express the DET in *E. coli*, and to transform Bacillus cells and express the full length structural *B.t.* DET in Bacillus cells. Because df the presence of a single Bam HI site in the multiple cloning site of pUC18, and the change of the EcoRI site opposite the multiple cloning site to a Bam HI, a single Bam HI endonuclease digestion will enable removal of virtually all of the pUC DNA after amplification of the vector DNA in *E. coli* if desired. This step is followed by isolation of the larger Bam HI fragment containing pBC16.1 and DET coding and regulatory sequences, religation to form a closed circle and transformation directly into Bacillus.

This DET expression plasmid, pBt1000 may also be used in the construction of similar plasmids containing mutant DET genes. Any of the full length mutant sequences described in said pending U.S. patent application Ser. No. 07/160,233 and published foreign counterparts may be readily prepared and used. For example, the 2.6 kb Mlul/Spel fragment of pBT-98c1 or pBT26-3 may be ligated with the 7 kb Mlul/Spel fragment of pBT1000. Plasmids constructed from such mutated sequences are described in more detail in the Example 4, hereinafter.

Any of the above plasmids, or others constructed to contain a DET DNA sequence, (with associated regulatory sequences) *E. coli* ori and *B.t.* ori, may be used to transform an *E. coli* host, by procedures well known in the art, such that amplification of the total DNA is effected, such that large quantities of covalently closed circular DNA for the subsequent transformation of a Bacillus host can be prepared from the transformed *E. coli* cells.

Transformation Procedures

Procedures for the transformation of Bacillus cells, eg. *B.t. kurstaki*, are already known such as described in U.S. application Ser. No. 136,880, filed Dec. 22, 1987 (which has a counterpart in British Application 86/30527, filed Dec. 22, 1986). Electroporation has been shown to increase transformation efficiency in *E. coli* to greater than $10^9$ colonies per ug of DNA, and has been reported to work for a wide variety of cell types and cell lines, including *B. subtilis* and *B. cereus* although at lower efficiencies. The improved process described herein allows transformation of *Bacillus thuringiensis* at a high efficiency, eg. an order of at least $10^6$ transformants per ug of DNA.

Cell types suitable for transformation by process of this invention include cry minus types such as the known *B.t.k.* cry 3B cells which have no plasmids and wild type Bacillus cells such as the native *B.t.* cells which carry endotoxin producing plasmids. As is well known in the art, Bacillus cells characteristically produce endotoxin in desired amounts only at their sporulation stage, and hence are grown to such stage in order best to obtain the products useful as insecticides. Hence, the plasmids containing DNA encoding a DET may be incorporated into Bacillus cells which are either devoid of endotoxin producing plasmids or already contain one or more of such plasmids. Bacillus cells transformed with plasmids are grown up by standard techniques and the recovered spore/endotoxin biomass may be used directly as insecticides in a manner known to the art.

The electroporation and recovery of cells in accord with the invention is carried out with cells while in a hypertonic state. For such purposes, three basic steps are desirably carried out involving: a) growing the cells in a hypertonic aqueous medium; b) subjecting the cells to electroporation in the presence of the desired exogenous DNA while maintaining the hypertonic status; and c) isolating and resuspending the thus treated cells in hypertonic aqueous media and growing for eg. 2 hours, to obtain intact cells (which are capable of normal growth), and to express antibiotic resistance genes. Step a) may be omitted but is highly preferred.

The electrotransformation used in this invention is a process which may be carried out with a GENE PULSER™ electroporation apparatus (Bio-Rad Laboratories, Richmond, Calif.), in a manner generally consistent with the operation of such apparatus. In electroporation a brief, high voltage pulse is passed through a suspension of cells and DNA to be transformed to effect the transformation. The general conditions for conducting electrotransformations with such apparatus are known. The voltage desired to be employed will generally vary with capacitance, and a capacitance setting of 3 μF may be used with the apparatus. Voltages useful step b) in our process may vary from about 1500 to 3000, more suitably 1700 to 2700 and preferably 1900 to 2600, depending upon cell density. The total time of pulse charge is no more than a few milliseconds and automatically determined from the voltage/capacitance setting on the Gene Pulser™ apparatus and the resistance of the sample. Optical density (O.D.) of the cells at harvest time for electroporation may vary but will be usually 0.1 to 0.8. While densities of 0.2 to 0.5 may be suitably employed, it has been found that a density of 0.55 to 0.8, particularly 0.6 to 0.75, may be very satisfactorily employed and combined with higher voltages, eg. 2200 to 3000, preferably 2300 to 2600 (or to 2500 which represents to unmodified limit of the apparatus above indicated). During electroporation itself, the cells (in tubes) are kept on ice, eg. at a temperature of 0° C. to 5° C. The amount of DNA used in the transformations is generally between 50 ng to 5 ug per 800 ul. of cells, more usually 100 ng. to 4 ug., and preferably 0.5 ug to 2.0 ug. per 800 ul. of cells.

In general, in steps a), b) and c), the desired hypertonic status may be achieved by any of a variety of compounds which do not pass the semi-permeable cell membrane and which are not metabolized by or toxic to the cells. The saccharides, particularly mond- and disaccharides, are quite suitable, preferably sucrose and lactose, more preferably sucrose. The concentration of saccharides, eg. sucrose, employed is suitably of the order of about 0.35M saccaride per liter of aqueous media or higher, to provide concentrations which are essentially isotonic with respect to the cell cytoplasm. Such osmotic status is in general preferably obtained with a concentration of from 0.35M to 0.55M of saccharides per liter of media, more preferably 0.38M to 0.52M of saccharide, eg. sucrose, per liter. The hypertonic aqueous media should be essentially neutral, ie. have a pH of from 5 to 9, preferably 6 to 8, with buffers being generally used for such purpose. Other ingredients such as conventional nutrients and salts may be included in the hypertonic media.

Cells may be prepared for transformation in step a) by growing in conventional manner, eg. with aeration and a temperature which usually between 20° C. to 40° C., preferably 20° C. to 38° C. (eg. 37°C.). Desirably, growth is effected in an appropriate hypertonic nutrient medium, such as Brain Heart Infusion (BHI) with 500 mM sucrose, to exponential phase as measured by 0. D. 600 nm of 0.1 to 0.8, eg. 0.2 to 0.5 but more preferably to 0.6 to 0.8. Lysozyme may be added to the culture, but the process may be operated to produce very good results without lysozyme and especially when the higher cell concentrations are used. The cells are concentrated by centrifugation resuspended in ice cold hypertonic buffered solution (5 mM Hepes pH 7.0, 0.5M sucrose). The cells are concentrated further by repeated centrifugation/wash steps to a final concentration of the order of $10^8$–$10^9$ cells/ml. and stored on ice.

The amount of lysozyme, when employed, should be well less than that normally used for the preparation of protoplasts, e.g. an amount not in excess of about 500 micrograms per ml. of hypertonic media. Such amount (concentration) will of course depend on various factors such as the osmotic pressure of the medium, its temperature, the desired reaction time etc. In general a suitable lysozyme concentration is of 20 to 300 microgram, e.g. of 200 microgram per ml of hypertonic aqueous medium (which is substantially lower than the 2 to 15 mg per ml which would be normally required for protoplasting purposes). Adequate distribution of lysozyme in the cell culture medium is desirably maintained. The reaction time will i.a. depend on the concentration and the quality of the lysozyme solution employed. In particular, the optimum lysozyme reaction time prior to transformation may be determined by preliminary assay in which samples of *B.t.* cells in the hypertonic medium are treated with the same given amount of lysozyme and individual such samples subjected to the same amount of lysozyme are reacted for different times. Preferably, the lysozyme is added to its final concentration at a lower cell concentration of about 0.2 to 0.3 and the lysozyme-treated cells are harvested after 30 minutes at an O.D. of 0.4 to 0.5 for use in electrotransformation.

In the electroporation step b), above, aliquots of buffered cells (eg. 800 ul) are mixed with the DNA, eg. vectors, to be transformed into the cells, and the suspension subjected to the pulsing at the desired voltage and capacitance settings until the apparatus signals discharge (audible beep with Gene Pulser™).

Following electrotransformation, the suspension comprising the transformed cells is then worked up in Step c), above, employing conventional methods but while securing the hypertonic status of the cells (when in solution/suspension). Thus the suspension is for example diluted in BHI/0.5M hypertonic medium and incubated. The suspension is incubated at a temperature of 20° to 40° C., e.g. at 37°. The suspension is conveniently gently aerated (150 rpm) employing e.g. a shaking water bath. The required incubation is relatively short and generally need be carried out only for a time sufficient to allow expression of an antibiotic resistance gene carried by the exogenous DNA for the anti-biotic resistance to be used to identify the transformed cells, or the expression of other marker genes incorporated for similar purposes. Such incubation also allows for whatever time may be needed for the treated cells to recover their ability to grow normally in Luria medium. Generally, the incubation is carried out for a period of at least about 60 minutes. An appropriate incubation time is no more than about 5 hours. Longer times may be employed but offer no particular advantage. Hence, incubation times are usually between 60 minutes to 5 hours, more preferably between 1.5 to 4 hours, e.g. 2 hours. After such incubation, the freshly prepared cells may be identified in a conventional manner and are capable of normal growth in Luria (normal) media similar to that of the untransformed parent cells.

Further, in accordance with the invention, transformation frequencies are further enhanced by transforming the *B.t.* cells with DNA which has been obtained from cells of the same subspecies type and character as the cells to be transformed. Such improvement, herein "homologous conditioning", may be due to minor adaptions, such as DNA methylation patterns, which particular cell types impart to heterologous DNA taken up by the cells, thereby making the DNA more subject to transformation back into the same cell type. In any event, when the DNA, eg. plasmids, vectors and the like, to be transformed into the ultimate *B.t.* host are constructed or amplified in a different host, it has been found desirable to transform the recovered DNA into cells of the same subspecies (preferably strain) to be ultimately or later transformed, recovering the DNA from said subspecies and then use the recovered DNA to again transform said subspecies, whereby distinctly higher frequencies of transformation may be obtained. When the ultimate host is a different strain (or mutant) of the same subspecies used as an intermediate host, similar type benefits may be obtained by transforming the ultimate host and collecting the resulting homologous conditioned DNA for again transforming the ultimate host cells. One advantage of such conditioning procedure is that DNA conditioned in a desired host can be mutagenized or otherwise altered after such conditioning and then transformed at distinctly high frequencies back into the same subspecies (or strain), thereby substantially improving mutasenisis procedures by avoiding less similar hosts and/or low frequency transformations as otherwise required to amplify the DNA or obtain the final product. Such conditioning may be used to advantage in mutagenizing by simply transforming a host, eg. a *B.t.*, culturing, recovering the DNA, mutagenizing, and transforming the mutagenized DNA into a host of the same species, subspecies or strain, particularly the same subspecies.

It has also been found that the intermediate transformation of *B.t.* hosts capable of being transformed in good frequencies can be an important factor in enabling other, more difficult to transform *B.t.* hosts to be satisfactorily transformed, particularly with larger vectors carrying a *B.t.* endotoxin gene and/or DNA adapted for desired functioning or expression in different hosts, e.g. so-called shuttle vectors. For example, *B.t. aizawai* has been found very difficult to transform, particularly with the larger vectors. Difficulties have also encountered *B.t. tenebroinis* (also *B.t. San Diego*). For example, such DNA vectors when amplified and recovered from *E. coli* could not be transformed in our experience into *B.t. aizawai* or *B.t. tenebrionis* with sufficient frequency to enable the identification of positive isolates. However, when the *E. coli* derived DNA was first transformed into *B.t. Kurstaki*, other DNA recovered from *B.t.K.* could then be transformed into *B.t. tenebroinis* with high frequency. However, the same DNA recovered from *B.t. kurstaki* could not be successfully transformed into *B.t. aizawai* but it was found that the same DNA recovered from *B.t. tenebroinis* could be transformed into *B.t. aizawai* in high frequency. Hence, the invention also provides a process for transforming *B.t.* cell hosts, particularly the more difficult to transform hosts such as *tenebrionis* and *aizawai*, with DNA amplified in *E. coli*, said process comprising transforming at least one intermediate, *B.t.* host which is a different subspecies or strain than the ultimate host, and transforming the ultimate *B.t.* host with the DNA recovered from the last to be transformed intermediate host. In another aspect, DNA recovered from *B.t. tenebroinis* is directly used to transform *B.t. aizawai.* In another aspect, DNA recovered from a *B.t. kurstaki* is directly used to transform *B.t. tenebrionis*. In general, DNA more easily transformed into one *B.t.* host than other *B.t.* subspecies or strain host may be transformed into the easier transformed host to condition the DNA prior to transforming the more difficult to transform *B.t.* host. Such conditioning transformations are particularly applicable to larger plasmids containing truncated or full length endotoxin genes along with other DNA such as origin of replication and an anti-biotic resistance gene, and essentially to shuttle vectors which comprise at least two origins of replications to allow for replication in at least two different hosts, eg. *E. coli* and *B.t.*, and which may contain other DNA for a second or additional hosts such as promoter, RBS and other operator sequences and/or a second gene for another anti-biotic resistance operable in a second or additional host. In general, the conditioning is effected simply by transforming a host, allowing for recovery as necessary to provide intact cells and culturing the cells to any volue desired or practical to recover the DNA for the subsequent or ultimate transformation.

Such DNA may also be conditioned for transformation into more difficult to transform *B.t.* hosts or at high frequencies into *B.t.* hosts by transforming, constructing and/or amplifying the DNA in certain *E. coli* hosts such as those identified as GM31 and GM2163, both of which are available from New England Biolabs, Beverly, Mass. We have, for example, successfully transformed both *B.t. tenebroinis* and *B.t. aizawai* with endotoxin-gene carrying shuttle vectors of the type described after amplifying the vectors in GM2163.

EXAMPLE 1

Preparation of plasmid pUC:BiB

A. Several micrograms of pBC16.1 DNA were digested with EcoR1 endonuclease and the linearized DNA gel isolated away from any remaining undigested plasmid DNA and/or contaminating chromosomal DNA. An aliquot of this purified 2.9 kb EcoR1 fragment was ligated into DNA prepared the same way by digesting pUC18 with EcoR1. A control reaction of self-ligated pUC18 EcoR1 linearized DNA was used. Aliquots from these two ligations were used to transform competent *E. coli* host JM105. Cells were spread onto Yeast/Tryptone (YT) agar plates containing ampicillin, IPTG (isopropylthiogalactoside) and XGal. The IPTG/XGal selection allows for a colorimetric screening of insert containing pUC18 plasmids (white) due to the interruption of the Lac Z gene in the multiple cloning site of pUC plasmids. The control plates (no insert pBC16.1 DNA) showed less than 1% white colonies (background level). The experimental plates (pUC+pBC16.1 ligation) showed 20% white colonies. Six white colonies were picked from the experimental transformation plate and used to inoculate YT liquid media containing 50 ug/ml ampicillin and grown overnight at 37 degrees celcius with shaking. Plasmid DNA mini-preparations were done ohi the six cultures and the DNA was analyzed by digestion with EcoR1. The pattern for all 6 clones indicated the presence of a 2.7 kb pUC18 band and a 2.9 kb pBC16.1 band. Further analysis with other restriction enzymes indicated both orientations of the inserted pBC16.1 plasmid had been obtained, as expected. These clones were named pUC:B 1 through 6.

B. To evaluate whether pUC:B DNA would replicate autonomously in *B.t.*, a large scale plasmid preparation of pUC:B was done and purified on a cesium chloride gradient. This DNA was used to transform *B.t.* cryB cells by electroporation as described by this invention report. Tetracycline resistant colonies were obtained and plasmid DNA was isolated. Restriction enzyme analysis confirmed pUC:B DNA was unaltered and could be used to re-transform competent *E. coli* or *B.t.* cells.

C. Formation of pUC:BiB: PUC:B was subjected to a partial digestion with EcoR1 and the overhangs thus produced on the linear molecule were filled in with DNA polymerase 1 Klenow fragment and dNTP's. The Bam Hl linkers shown below were purchased from New England Biolabs for ligation with the filled-in vector ends.

| | |
|---|---|
| 5'CGGGATCCCG3'<br>3'GCCCTAGGGC5' | Bam H1 10mer |

The BamHl linker was present in the ligation reaction at a 50 fold molar excess compared to the pUC:B vector. Aliquots of this ligation were used to transform competent *E. coli* JM105 and clones were selected on YT agar plates containing 50 ug/ml ampicillin. Mini plasmid DNA prep. and restriction enzyme digestion confirmed the presence of the inserted linker at the previous EcoR1 site in 15% of the clones examined. The new plasmid containing this inserted BamHl site is named pUC:BiB and is shown in FIG. 1.

EXAMPLE 2

Preparation of plasmid pBEV210-TL

A. Plasmid pk8-1 was digested with Hpal and Sstl and the 1.5 kb fragment to serve as an insert in a subsequent ligation reaction was gel isolated and purified. Plasmid prAK was digested with Nrul and Sstl to isolate a 3.9 kb prAK fragment to serve as a vector. Equimolar amounts (0.5 pmole) of the 1.5 kb Hpal/Sstl pk8-1 fragment and the 3.9 kb Nrul/Sstl fragment were ligated together in a 20 ul reaction volume. 4 ul of this experimental ligation was used to transform competent *E. coli* strain JM105 and colonies were selected on YT/amp. plates. The number of transformants on the experimental plate was approximately 100 fold greater than control experiments with vector religated in the absence of the pk8-1 insert.

Six colonies from the experimental plate were grown in liquid culture for DNA preparation and restriction enzyme analysis. Ndel restriction enzyme was used and 6 out of 6 clones examined had the correct pattern (three fragments, 4211 bp, 737 bp and 409 bp). This clone is referred to as pBEV100.

B. Formation of plasmid pBEV210: 5–10 ug of pBEV-100 and pBT210 DNA were each digested with Hpal and Sstl. The 1.6 kb Hpal/Sstl fragment from pBEV100 (insert) and the 6.9 kb Hpal/Sstl fragment of pBT210 (vector) were gel isolated and purified by standard techniques. The fragments were ligated together using a 4:1 molar ratio of insert to vector. *E. coli* strain JM105 competent cells were transformed with this ligation and colonies were selected on 20 ug/ml Chloramphenicol plates. Fourteen of the colonies were cultured from the experimental plate for DNA mini-prep. and restriction enzyme analysis. All 14 clones were shown to have the correct banding pattern when digested with Hpal and Sst 1 (6.9+1.6 kb). One of these colonies was cultured for a large scale plasmid preparation and was called pBEV210, and is illustrated in FIG. 2.

C. To insert the *B.t.* DET 3' transcription termination loop into our pBEV210 clone, complementary oligonucleotides containing this DNA sequence as well as Pvul ends for cloning were designed and purchased from Research Genetics, Inc.

SMA I
5' AAAACGGACATCACCTCCATTGAAACGGAGTGATGTCCGTTTTCCCGGGAT 3'
3' TATTTTGCCTGTAGTGGAGGTAACTTTGCCTCACTACAGGCAAAAGGGCCC 5'
PVU I "STICKY ENDS"

The oligonucleotides were first 5' phosphorylated with T4 polynucleotide kinase as described by Maniatis (1982 Cold Spring Harbour Laboratories, New York, MOLECULAR CLONING, A LABORATORY MANUAL). These oligonucleotides were annealed by placing them, in an equimolar ratio, in a heating block at 100 degrees celcius for five minutes. The block was then turned off and the temperature allowed to fall to 30 degrees celcius over a one and a half hour period, placed at room temperature for 5 minutes, and on ice for 5 minutes. Self-ligation of the annealled oligonucleotides was done and a ladder was visualized on a 2% agarose gel.

pBEV210 was prepared by partial PvuI digestion. 10–20 ug of pBEV210 was digested with PvuI for 5–10 minutes at 37 degrees celcius to obtain the linear DNA. This DNA was isolated on a 1% preparative agarose gel, eluted and purified according to standard procedures. The 8.6 kb linear pBEV210 vector was ligated with a 200 fold molar excess of the oligonucleotide cassette encoding the RNA transcription termination loop. JM105 competent *E. coli* cells were transformed with an aliquot of the ligation and the cells were plated onto YT/chloramphenicol for selection.

Thirteen colonies were selected from the experimental plate for DNA mini prep. and restriction enzyme analysis. Six of the 13 clones were shown to contain the inserted oligonucleotide based on the presence of the Sma 1 site internal to the oligo cassette. To check for the correct orientation of the inserted oligonucleotide, ScaI enzyme was used to digest these six clones along with SmaI. There is a ScaI site at the very 3' end of the DET gene in pBEV210. If the oligonucleotide was inserted in the proper orientation, a ScaI/SmaI digestion would give a 310 bp fragment. One of the six potential clones showed this fragment and it was designated pBEV210-TL (FIG. 2).

EXAMPLE 3

Preparation of plasmid pBT1000 pBEV210-TL DNA was digested with the restriction enzymes HpaI and SmaI and the 4 kb fragment thus produced was gel isolated and purified for use as an insert in a subsequent ligation. The vector pUC:BiB was digested with SmaI to produce a linear fragment of 5.6 kb. These two fragments were ligated with a five fold molar excess of insert to vector. Aliquots of this ligation mixture were used to transform competent *E. coli* strain JM105 and colonies were selected on YT/agar plates containing 50 ug/ml ampicillin.

Figure 3:
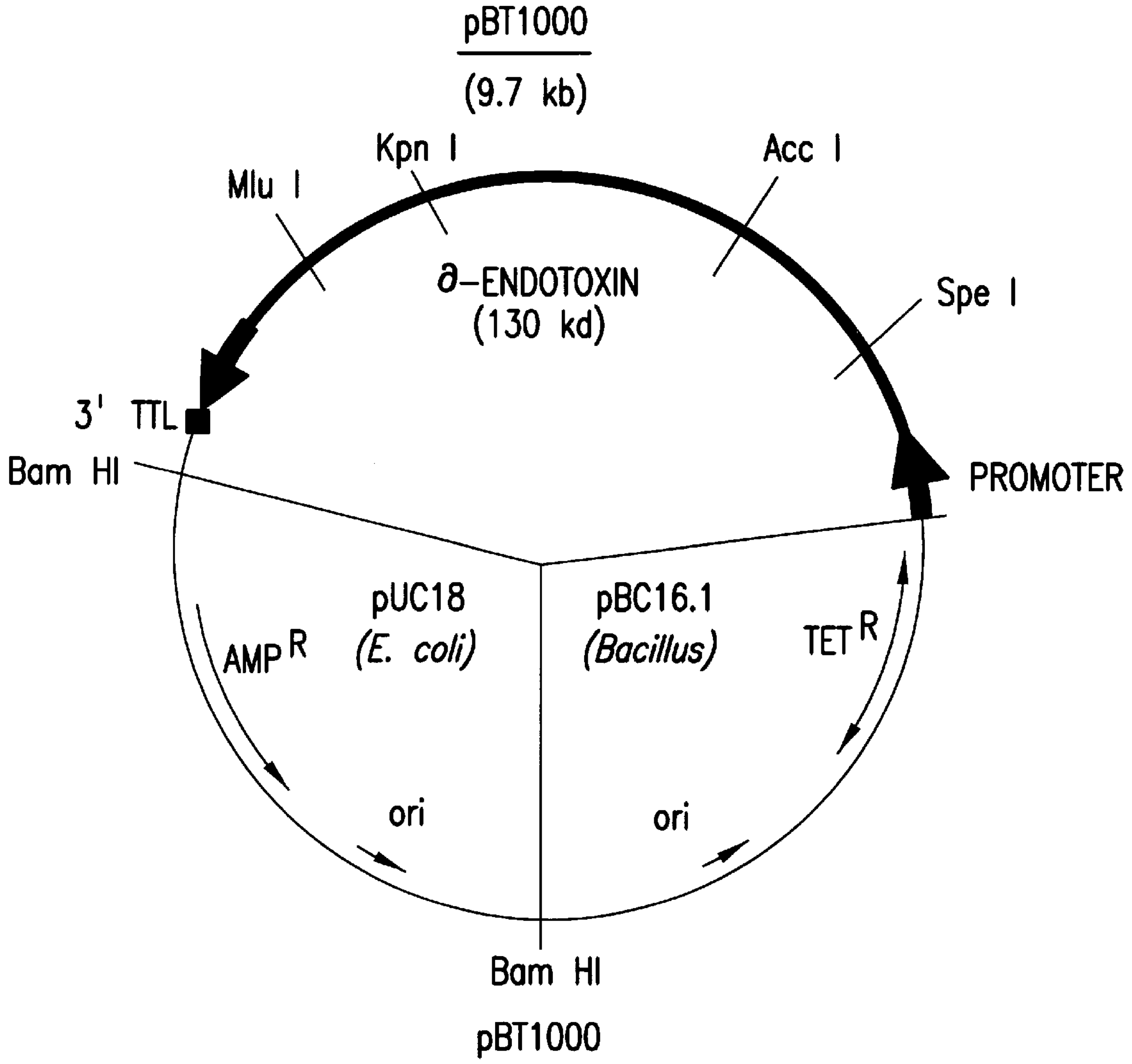
FIG. 3: illustrates the expression vector pBt1000.

Transformants were replica plated onto YT/amp plates and colony lifts onto nitrocellulose membranes were done. The clones were screened for the presence of the DET gene by hybridization with a 32-P radiolabelled SpeI/MluI DNA fragment of the DET gene. Positively hybridizing clones were further analyzed by DNA mini preps and restriction enzyme digestion. The results indicated that positive clones had been produced with the DET gene inserted into the PUC:BiB vector in both orientations as expected. The resulting clone, pBT1000 had the desired orientation and is shown in FIG. 3.

EXAMPLE 4

Preparation of *B.t.k.* up-mutant plasmids

Ligations were performed between the 7 Kb MluI-SpeI fragment of pBt1000 (gel isolated and purified) and the following mutation containing DNA fragments isolated from mutant DET clones (see also USSN 160,233 for mutant identifications):

a) 2.6 Kb MluI-SpeI fragment of "C" in pBT210 (forms pBT 1001)

b) 2.6 Kb MluI-SpeI fragment of "26-3" in pBT210 (forms pBT 1002)

c) 2.6 Kb MluI-SpeI fragment of "36a65" in pBT210 (forms pBT 1003)

d) 2.6 Kb MluI-SpeI fragment of "S" in pBT210 (forms pBT 1004)

e) 2.6 Kb MluI-SpeI fragment of "98c1" in pBT210 (forms pBT 1005)

The ligations were transformed into *E. coli* JM105 and, in all cases, the transformation numbers were at least 10 fold higher for vector and insert than for religated vector alone. Transformants were screened by DNA mini-preps and MluI-SpeI restriction enzyme analysis and the presence of the inserts confirmed. DNA sequence analysis confirmed the correct point mutations were present for a positive clone from each of the five ligations listed above.

EXAMPLE 5

Transformation of *Bacillus thuringiensis*

A GENE PULSER™ transfection apparatus was purchased from Bio-Rad Laboratories. Reports in the literature on transformation of other cell types showed maximal efficiency occurred at a cell survival rate of approximately 50%. We selected this survival rate for our initial attempt at transformation and set up the following experiment to determine which voltage setting would give us this level of viability. Initial procedures used were those known to be effective for transformation of *Bacillus subtilis.*

A 100 ml culture of *B.t.* cry B was grown in Brain Heart Infusion (BHI) media purchased from Difco Laboratories to an optical density of 0.5 measured at 600 nm. Cells were sequentially pelleted by centrifugation at 4000 rpm for 10 minutes and resuspended in equal volume, 50% volume, 25% volume, and 12.5% volume of 10 mM ice cold Hepes buffer pH7.0. In the end, the cells have been concentrated 8 fold and are in 10 mM Hepes buffer pH7.0 Aliquots containing 800 ul of this cell suspension were transferred into special sterile cuvettes supplied by the manufacturer. A cuvette containing these cells was then inserted into the holder and pulsed at one of the selected voltages, with the capacitance setting remaining constant at 3 uF. Voltage settings used to generate a cell survival curve were 1300 V, 1500 V, 1700 V, 1900 V, 2100 V and 2300 V.

After pulsing, the cells were serially diluted by a factor of $10^5$ in sterile BHI media. Aliquots of the final dilution were plated onto YT/agar and incubated at 37° C. for 10 hours. A control aliquot of cells which were diluted in the same manner but not pulsed was used to calculate the 100% survival value.

Figure 4:
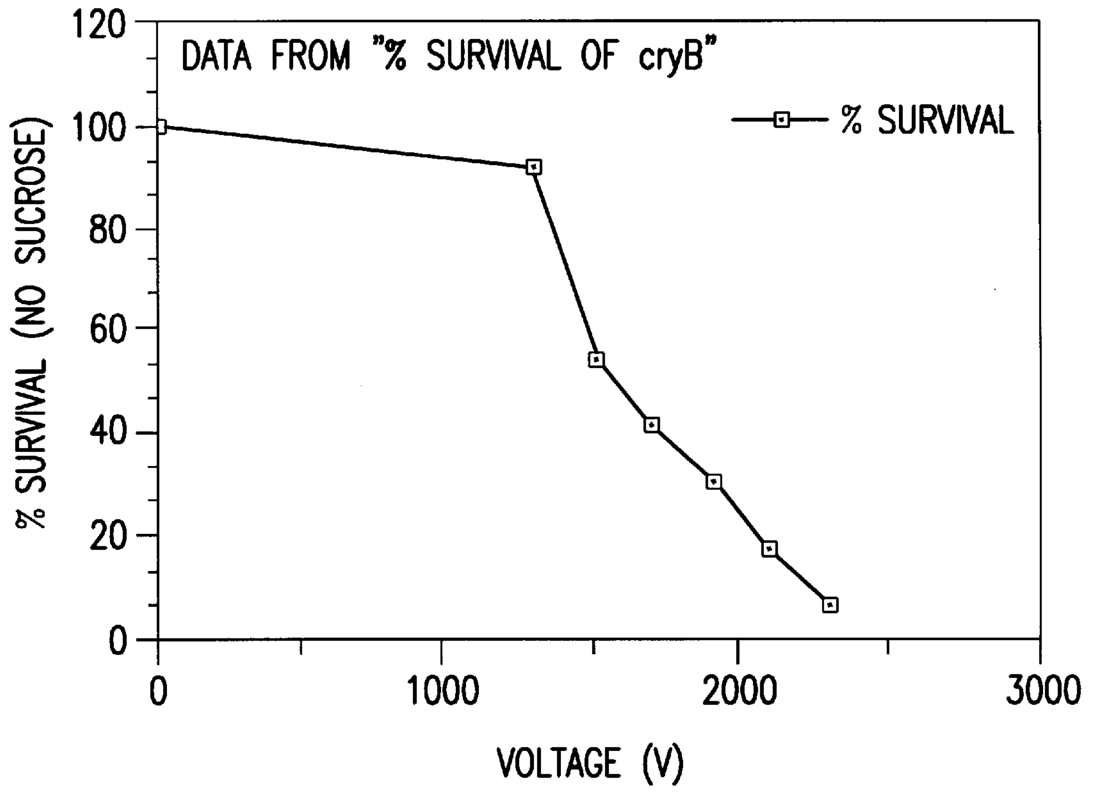
FIG. 4: represents a graph showing percent survival vs. electrotransformation voltage applied for transformation of *B.t.* crystal minus cells (Cry B).

The number of colonies surviving each experimental voltage setting was divided by the number on the control plate to calculate percent survival. All settings were done in duplicate. The results indicated that a 50% survival was seen at approximately 1950 volts, as shown in FIG. 4. Using this as our starting point, Cry B cells were prepared as described above and pulsed with 5 μg of pUCBiB DNA. After pulsing, cells were transferred into 10 mls sterile BHl media in 50 ml conical tubes and incubated at 37° C. for 2 hours to allow for recovery and expression of tetracycline resistance. Following recovery, the cells were concentrated by centrifugation at 4000 rpm for 10 minutes. The pellet was resuspended in 500 μl YT media and plated onto two YT/agar plates containing 20–40 μg/ml tetracycline and incubated at 37° C. overnight. A control experiment (minus DNA) was carried out in parallel.

Efficiencies of approximately 100 tetracycline resistant colonies were obtained per μg of DNA, demonstrating the efficacy of this approach with *B. thuringiensis* cells. Mini plasmid DNA preparations were done according to standard procedures. The isolated DNA was analyzed by restriction enzyme digestions, and both the identity and integrity of the plasmid DNA were confirmed. We subsequently attempted to transform cry B cells with pBT1000 DNA using these same conditions. We were able to obtain positive clones, although at ten-fold lower frequencies than our results with the vector pUCBiB DNA. The predicted patterns from various digestions of mini-prep DNA from positive cry B transformants confirmed both the presence and integrity of pBT1000 DNA.

Figure 5:
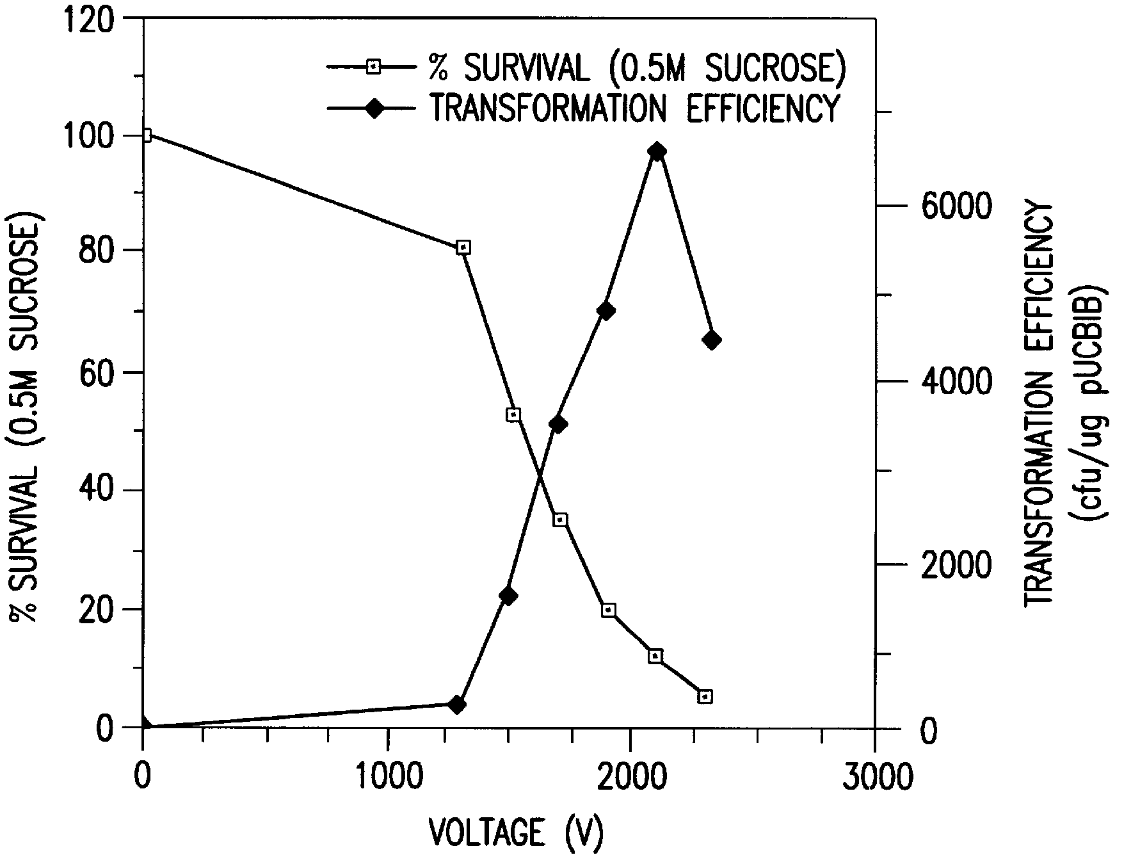
FIG. 5: represents a graph showing percent survival vs. electrotransformation efficiency of Cry B cells.

We wanted to directly examine percent cell survival versus efficiency of transformation to see if in fact 50% survival is optimal. Cells were prepared as described above and plated onto selective and non-selective media. The number of colonies from a control aliquot (non-pulsed, plated on non selective media) was taken as the 100% survival value. Colonies on YT media from samples pulsed at various voltages were counted to calculate % survival. Likewise, colonies on tetracycline-containing plates were counted to determine transformation efficiency. The relationship between cell survival and transformation efficiency is shown in FIG. 5, for cells grown to OD600 of about 0.4.

To analyze expression of DET in pBT1000 cryB transformed strains, (cry 1000), a 30 μl aliquot from an 18 hour culture was mixed with one quarter volume of sample buffer, heated at 100° C. for 10 minutes and electrophoresed on a 9% SDS polyacrylamide gel. Control lanes of pUCBiB-transformed cells as well as molecular weight standards were included. Following electrophoresis, proteins were visualized by staining with Coomassie. Western blot analysis confirmed that the 130 Kd protein was immunoreactive to DET polyclonal antisera. Using gel scanning densitometry measurements, the level of DET expression in cry1000 strains was estimated to be 30% of the total cellular protein when culture conditions were optimized.

EXAMPLE 6

Highly efficient transformation of *B.t.* using improved electrotransformation procedures. Several approaches were taken to improve the efficiency of *B.T.* electrotransformation.

EXAMPLE 6A

Lysozyme/Sucrose

Shown below are results we obtained after modifying the procedure to include lysozyme and sucrose. Differences between the previous procedure of Example 5 and a procedure involving lysozyme and sucrose are indicated below.

| Parameter | Previous | Current Lysozyme/Sucrose |
|---|---|---|
| Media | BH1 | BH1/0.5 M sucrose |
| Temp. | 37° C. | same |
| O.D. @ Harvest | 0.4–0.5 | same |
| Lysozyme | none | 200 μg/ml, 30 min. |
| Washes/resuspension for transformation | 10 mM Hepes pH 7.0 | 5 mM Hepes pH 7.0, 0.5 M sucrose |
| Pulse | 1950 V/3 μF Cap. | 2000 V/3 μF Cap. |
| Recovery | 3 hrs. in BH1 | 2 hrs. BH1/0.5 M suc. |
| Selection | 20 μg/ml TET followed by 50 μg/ml | same |

Electrotransformation of cryB *Bacillus thuringiensis* cells using the previous conditions gave efficiencies of $10^2$ colonies per μg of pUCBib DNA. By modifying the procedure to include gentle lysozyme treatment in hypertonic growth media, we were able to get repeatable efficiencies of $10^4$ colonies per μg pUCBiB and $10^3$ per ug for pBT1000 when these plasmids were prepared from *E. coli* hosts, or a 100 fold enhancement over our initial results.

EXAMPLE 6B

Effect of DNA Source

A crystal plus Javelin® substrain of *B.t. kurstaki* H.D. 562, herein also "SA11", was transformed with pBT1000 as described above for cryB to form strain SA1000. Similar transformation efficiencies were seen with this strain as were obtained for *B.t.* cryB ($10^4$ per ug of DNA for pUCBiB and $10^3$ per ug for pBT1000).

We examined what effect the source of DNA had on determining our efficiencies. Two strains of *B.t.*, cry B and SA11, were transformed with DNA isolated from *B.t.* cry B, *B.t.* SA11, and *E. coli* JM105. In all cases, the lysozyme/sucrose method was used as described above. DNA concentration and extent of supercoiling were controlled for and the only variable in these experiments was the host cells from which the DNA was prepared. Results from reciprocal experiments (some done in duplicate) for transformations with pBT1000 DNA are given below:

| Strain Transformed | DNA Source | # of CFU's |
|---|---|---|
| Cry B | SA11 | $1.4 \times 10^3$, $1.8 \times 10^3$ |
| Cry B | Cry B | $1.5 \times 10^5$, $1.9 \times 10^5$ |
| Cry B | *E. coli* | $2.5 \times 10^3$ |
| SA11 | Cry B | $6.4 \times 10^3$ |
| SA11 | SA11 | $1.3 \times 10^5$ |
| SA11 | *E. coii* | $1.3 \times 10^4$ |

The results shown above indicate a significant preference for homologous DNA in *B.t.* transformations. This effect is likely due to differing patterns of DNA methylation recognized by each host.

EXAMPLE 6C

High Efficiencies with modified Transformation Procedure

A procedure carried out similar to that of Examples 5 and 6A obtained high efficiencies by growing cells to a higher density, and without using lysozyme. Differences between this modified procedure and the lysozyme/sucrose procedure are shown below.

| Parameter | Lysozyme/Sucrose (Example 6A) | Higher OD without Lysozyme |
|---|---|---|
| Media | BH1/0.5 M Sucrose | same |
| Temp. | 37° C. | same |
| OD at Harvest | 0.4–0.5 | 0.66 |
| Lysozyine | 200 μg/ml. 30 min. | none |
| Washes/ resuspension for trans- formation | 5 mM Hepes pH 7.0 0.5 M Sucrose | same |
| Pulse | 2000 V/3 μF | 2500 V/3 μF |
| Recovery | 2 hrs. BH1/0.5 M sucrose | same |
| Selection | 20 μg/ml TET followed by 50 μg/ml | same |

In this Example 6C it was found that growing the cells to a higher OD600, eg. 0.6 to 0.8, over the course of an additional one hour could improve efficiencies by as much as 50 fold using sucrose but without adding lysozyme. By this procedure it was found that SA11 cells could be transformed in efficiencies of $5\times10^5$ colonies per μg. of pUCBiB and $1\times10^5$ colonies per μg. of pBT1000.

EXAMPLE 7

Toxicity of transformed *B.t.* strains Cry B and SA11

The following toxicity data (evaluation for insecticidal activity) were obtained by growing the *B.t.* cells to be evaluated in Dulmage medium for 4 days at 30° C. The amount of toxin present in each culture was equivalent as judged by SDS PAGE and scanning gel densitometry. Five different quantities of each cultured cell system to be evaluated were mixed in cups with artificial diet to provide a range of concentrations of from 0.12% to 10% expressed as a volume percent *B.t.* culture present. One second instar larvae was placed in each cup and each concentration was run 10 times (total 50 cups per culture). Percent mortality versus percent concentration were graphed and the lowest dose giving fifty percent (50%) mortality ($LD_{50}$ value) was calculated for each culture to be evaluated. Relative toxicities to pBT 1000 were also calculated for the pBT1000 series (pBT1000 to pBT 1006). The tables below indicate the results obtained. The Heliothis evaluated was *H. virescens* and the *spodoptera* evaluated was *littoralis*.

TABLE 1 pBt 1000 Series in Cry B - *H. virescens* and *Spodoptera littoralis*

| Plasmid | *H. Virescens* Relative to pBT 1000 (%) | *S. littoralis* Approximate $LD_{50}$ |
|---|---|---|
| pBT 1000 | 100 | 16.1 |
| pBt 1001 | 95 | 10.0 |
| pBT 4002 | 180 | 5.6 |
| pBT 1003 | 165 | NA* |
| pBT 1004 | 120 | NA* |
| pBt 1005 | 105 | NA* |
| pBT 1006 | 50 | NA* |

NA: Not active at highest concentration tested.

TABLE 2 pBT 1000 Series in SA11

| Plasmid | *H. virescens* Approximate $LD_{50}$ | *Spodoptera littoralis* Approximate $LD_{50}$ |
|---|---|---|
| pBt 1000 | 0.06 | 1.2 |
| pBT 1001 | 0.9 | 8.2 |
| pBT 1002 | 0.09 | 1.6 |
| pBT t003 | 0.15 | 3.75 |
| pBT 1004 | 2.2 | 9.1 |
| pBT 1005 | 0.1 | 1.4 |
| pBT 1006 | 1.2 | 10.1 |
| SA11 - control | 0.13 | 3.8 |

TABLE 2A

Certain pBT1000 Series Candidates in SA11 against Trichoplusia Ni

| Plasmid | $LD_{50}$ | Relative to SA11 (%) |
|---|---|---|
| pBT1000 | 0.47 | 87 |
| pBT1005 | 0.245 | 167 |
| SA11 - Control | 0.41 | 100 |

TABLE 3

Advanced Screening of PBT 1000 Series Candidates Relative to SA11
The following results were obtained after averaging the results of seven replications of the assay procedure described above.

| Plasmid in SA11 | *H. virescens* Relative to SA11 (%) | *S. littoralis* Relative to SA11 (%) |
|---|---|---|
| PBT1000 | ca 100 | 242 |
| pBT1002 | ca 100 | 313 |
| pBT1005 | 240 | 404 |
| SA11-Control | 100 | 100 |

The plasmid pBT1000 can be used to express hybrid DET genes. For example, the Spel/Kpnl fragment of a *B.t. kurstaki* DET gene of the cryl A(a) type (Hermon Hofte and H. R. Whiteley, Microbiological Reviews, June 1989, p. 242–55. Insecticidal Crystal Proteins of *B.t.*) contained in pES-1 (U.S. Pat. No. 4,467,036. Schnepf et al. Aug. 21, 1984.) can be inserted into pBT1000 digested with these same restriction enzymes. All of the amino acid changes within the active portion of the toxin genes contained in plasmids pES-1 and pBT1000 fall within a fragment defined by the restrictions enzymes Spel and Kpnl in common to both genes. The amino acids upstream of Spel are identical in both genes and tliose downstream of Kpnl are in the coding region of the inactive C-terminal portion of the protoxin. Our am was to replace the Spel/Kpnl fragment of the DET gene in our vector, pBT1000, with the corresponding fragment from the pES-1. The resulting clone has all of the DNA coding for the active portion of the DET from the cryl A(a) gene and a C-terminal portion of the DET gene from the cryl A(b) gene of *B.t.w*. Construction of this hybrid DET gene for expression in Bacillus and *E. coli* hosts is described in more detail in the following example.

EXAMPLE 8

Preparation of pBT 2000

Due to the occurrence of Kpnl sites elsewhere in the expression plasmid, we first cloned this hybrid gene into the vector pBEV210TL, as an intermediate step. Positive clones were then used to isolate the resulting hybrid DET gene for ligation into the *B.t.* expression vector. Details of these experiments are as follows:

The Spel/Kpnl 6.6 kb vector fragment from pBEV210TL and the Spel/Kpnl 2.0 kb insert fragment from pES-1were prepared from-the indicated plasmids by digesting 5 ug of each of pES-1 and pBEV210TL with 50 units of Spel and Kpnl for 3 hours at 37° C. Preparative agarose gels were run and the fragments were isolated and purified by DEAE disposable columns (Elutip). Ligations were set up with 0.06 picomoles (pmoles) of insert DNA and 0.02 pmoles of vector in a 20 microliter (ul) reaction volume. A control ligation was also set up containing 0.02 pmoles of vector in the same final volume. A 5 ul aliquot from each ligation was used to transform competent *E. coli* strain JM105 cells and transformed cells were selected on chloramphenicol plates (20 ug/ml). The ratio of colonies from the experimental vs. control ligation was greater than 50 to 1. Individual colonies from the experimental ligation were grown in liquid media with chloramphenicol (20ug/ml) for mini plasmid DNA preparation.

Plasmid DNA from twelve different isolates was prepared and analyzed by digestion with Pvu II. The kurstaki gene in pES-1 has a Pvu II site in the Spel/Kpnl fragment and lacks an Acc I site present in this region of the *B.t.w.* cloned DET gene. These differences distinguish between these highly conserved genes. Analysis of the fragment sizes produced with these two enzymes confirmed the desired hybrid DET clone, herein pBEV2000.

Figure 6:
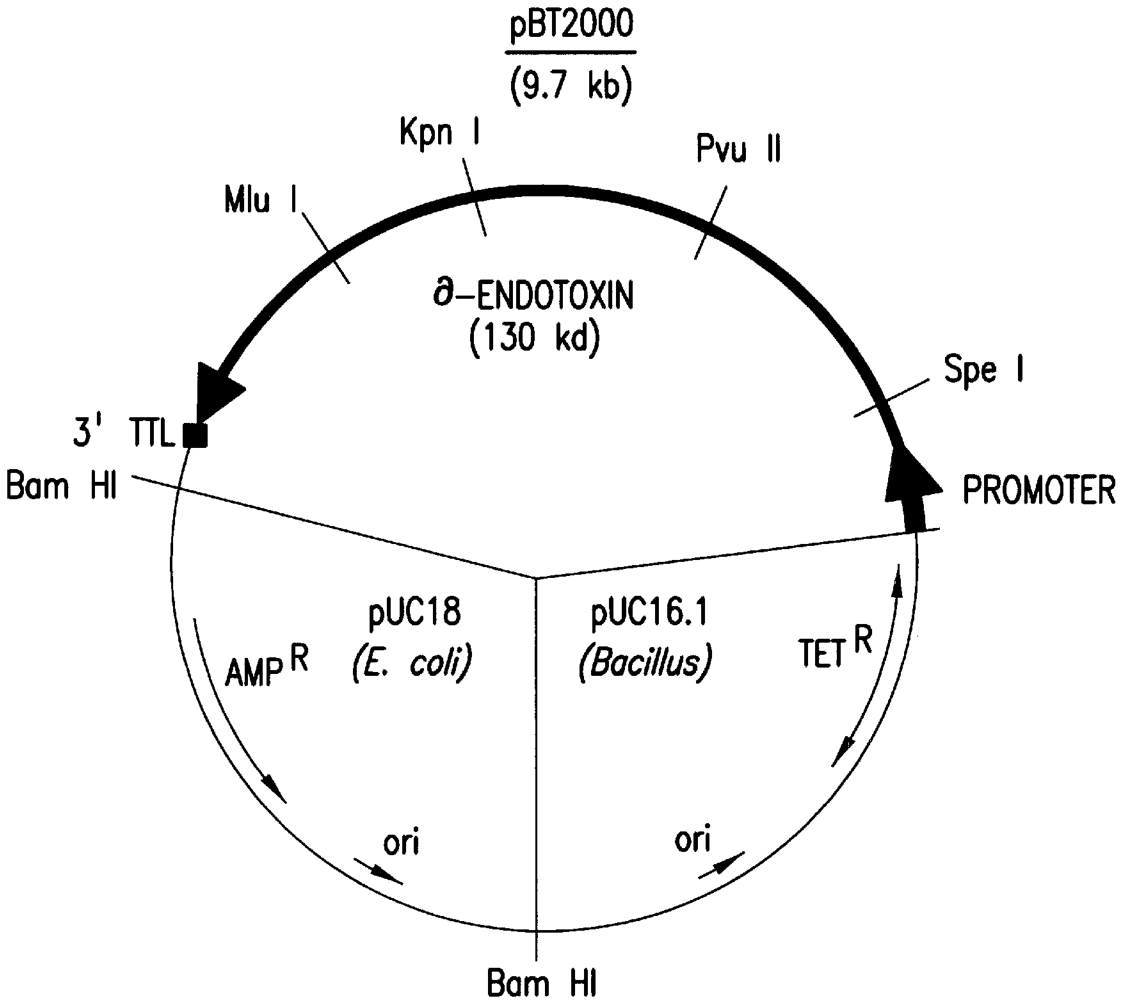
FIG. 6: illustrates the expression vector pBT 2000.

A large scale DNA preparation of pBEV2000 DNA was done to isolate a fragment containing the hybrid DET gene for cloning into our expression vector. The Spel/Mlul 7 kb vector fragment from pBT1000 and the Spel/Mlul 2.6 kb insert fragment from pBEV2000 were prepared, isolated and ligated as described above for pBEV2000. Plasmid DNA from resulting clones were analyzed by digestion with ACC I and PvuII enzymes. All six clones were confirmed as having the pES-1 gene up to codon 723 followed by the C-terminus from our 5.3 kb type gene and all regulatory (5' and 3') sequences present in our pBT1000 expression vector. This new clone was denominated pBT2000 and is shown in FIG. 6.

Initial attempts to transform *B.t. tenebroinis* with DNA prepared from *E. coli* were unsuccessful. High efficiencies ($10^5$ per ug DNA) were obtained when the DNA was first amplified in our transformed *B.t. kurstaki* strain SA1000. The resulting hybrid strain is referred to as TEN 1000. Likewise we were unable to isolate positive transformants of *B.t. aizawai* using pBT1000 DNA isolated from *E. coli* JM105 or strain SA1000, but *B.t. aizawai* could be transformed at a high efficiency when we isolated pBT1000 DNA from our Ten.1000 strain. In sumnary, we have discovered highly specific restriction/modification systems of different strains of *B.t.* which can be used to permit high efficiency transformation of crystal plus strains of *B.t.* (e.g. *B.t. kurstaki, B.t. aizawai, B.t. tenebrionis*). We have used this technology to produce the following hybrid strains:

SA1000 *B.t. kurstaki* strain transformed with pBT1000 [plasmid coding for the Cryl(A)b gene of *B.t. wuhanensis* (ref. *E. coli* mutant Patent Appl.].

Ten 1000 *B.t. tenebrionis* strain transformed with pBT1000 DNA.

Aiz 1000 *B.t. aizawai* strain transformed with pBT1000 DNA.

EXAMPLE 9

Assay of *B.t. aizawai*

*B.t. arzawai* (strain HD-137) transformed with pBT 1000 as indicated above was evaluated against *H. virescens* and *spodoptera* in a comparison against the native *B.t. aizawai* strain with the result that the transformed species (herein A12 1000) showed an $LD_{50}$ against the Heliothis of about 5.5 and against Spodoptera of about 18 while the wild type showed $LD_{50}$ values of about 3 and 4.5 respectively.

EXAMPLE 10

Assay of *B.t. tenebroinis*

*B.t. tenebroinis* transformed with pBT 1000 as indicated above (to produce TEN 1000) was evaluated against *H. virescens* and *Phaedon* (*cochleria*) in a comparison the native *B.t. tenebroinis* strain with the result that the native strain showed no practical affect against the Heliothis and the TEN 1000 showed 50% of the activity of the native strain against Phaedon but also showed an $LD_{50}$ of 8.39 against the Heliothis. In this example, the assays for Phaedon toxicity was a leaf disc assay in which the culture to be evaluated was sprayed directly onto leaf discs and allowed to dry. Ten insects ($2^{nd}$ instar) were then allowed to feed on the leaf discs for 7 days and toxicity then scored as percent mortality.

EXAMPLE 11

The plasmid pBT2000 was amplified in *E. coli* JM105, the DNA recovered and transformed by electroporotim as above described (using hypertonic media procedure) into *B.t.k.* SA11, the DNA recovered and transformed by electroporation as above described (using hypertonic media procedure) into *B.t. tenebroinis* to obtain transformed cell herein identified as TEN 2000. Plasmid DNA (pBT2000) was then recovered from TEN 2000 and transformed into *B.t. aizawai* (HD-137) by electroporation as above described (using hypertonic media procedure) to obtain transformed cells herein identified as AIZ 2000.

EXAMPLE 12

The transforants TEN 2000 and AIZ 2000 were evaluated for toxicity (unsectidal activity) by the assays above described with the following results.

A) B.t. tenebrionis cells

| Strain B.t. tenebrionis | Phaedon (% mortality) | Heliothis ($LD_{50}$) |
|---|---|---|
| TEN 1000 | 100 | 0 |
| TEN 2000 | 50 | 8.39 |
| TEN 2000 | 90 | 8.0 |
| Cry B/pBT 1000 (control) | 10 (background) | 8.07 |
| Cry B/pBT 2000 (control0 | 10 (background) | 11.56 |

B) B.t. aizawai cells

| Strain | Heliothis ($LD_{50}$) | Spodoptera ($LD_{50}$) |
|---|---|---|
| B.t. aizawai (HD-137) | 3 | 4.5 |
| AIZ 1000 | 5.5 | 18 |
| AIZ 2000 | 1 | 2.2 |

The above data indicates that AIZ 2000 is a very potent new *B.t.* strain with excellent potency towards both Heliothis and Spodoptera insects, and indicates the desirability of transforming *B.t. aizawai* with a plasmid expressing an endotoxin having an active toxic portion substantially the same or identical to the active portion (first 610 amino acids) of the pES-1 endotoxin (the amino acid sequence of which is described in Schnepf, et al., J. Biol. chem. Vol. 260 (1985), pgs. 6264–6272). The active portion of the endotoxin has at least about 50 amino acid differences from the *B.t.w.* active sequence and it is indicated that many changes or mutations in the pES-1 sequence, eg. as many as at least a majority or more of the 50 or more that differ, may be made while retaining the unexpected advantage over the parent *B.t. aizawai*, ie. greater activity against *H. virescens* and *exigua*, and all such mutants are considered within the invention.

The term "heterogenous" as used herein with reference to DNA and cells transformed therewith indicate that all or any portion of the sequence of the DNA is not native to or naturally found within the cells in question.

TABLE A

| | | | | | | | | | | | | | | |
|---|---|---|---|---|---|---|---|---|---|---|---|---|---|---|
| | | | (a) | | | | | | | | | | | −46 |
| | | GG | ATC | CGT | TTT | AAA | TTG | TAG | TAA | TGA | AAA | ACA | GTA | TTA |
| | | | Ile | Arg | Phe | Lys | Leu | * * * | * * * | * * * | Lys | Thr | Val | Leu |
| TAT | CAT | AAT | GAA | TTG | GTA | TCT | TAA | TAA | AAG | AGA | AGG | AGG | TAA | CTT |
| Tyr | His | Asn | Glu | Leu | Val | Ser | * * * | * * * | Lys | Arg | Trp | Arg | * * * | Leu |
| (−15) | | | | | | | | | | | | | | |
| | | | | | | | | | | | | | | 45 |
| ATG | GAT | AAC | AAT | CCG | AAC | ATC | AAT | GAA | TGC | ATT | CCT | TAT | AAT | TGT |
| Met | Asp | Asn | Asn | Pro | Asn | Ile | Asn | Glu | Cys | Ile | Pro | Tyr | Asn | Cys |
| (1) | | | (4) | | | | | | | | | | | (15) |
| TTA | AGT | AAC | CCT | GAA | GTA | GAA | GTA | TTA | GGT | GGA | GAA | AGA | ATA | GAA |
| Leu | Ser | Asn | Pro | Glu | Val | Glu | Val | Leu | Gly | Gly | Glu | Arg | Ile | Glu |
| ACT | GGT | TAC | ACC | CCA | ATC | GAT | ATT | TCC | TTG | TCG | CTA | ACG | CAA | TTT |
| Thr | Gly | Tyr | Thr | Pro | Ile | Asp | Ile | Ser | Leu | Ser | Leu | Thr | Gln | Phe |
| | | | | | | | | | | | | | | (b) |
| CTT | TTG | AGT | GAA | TTT | GTT | CCC | GGT | GCT | GGA | TTT | GTG | TTA | GGA | CTA |
| Leu | Leu | Ser | Glu | Phe | Val | Pro | Gly | Ala | Gly | Phe | Val | Leu | Gly | Leu |
| | | | | | | | | | | | | | | (60) |
| GTT | GAT | ATA | ATA | TGG | GGA | ATT | TTT | GGT | CCC | TCT | CAA | TGG | GAC | GCA |
| Val | Asp | Ile | Ile | Trp | Gly | Ile | Phe | Gly | Pro | Ser | Gln | Trp | Asp | Ala |
| | | | | | | | | | | | | | n−1 | |
| TTT | CTT | GTA | CAA | ATT | GAA | CAG | TTA | ATT | AAC | CAA | AGA | ATA | GAA | GAA |
| Phe | Leu | Val | Gln | Ile | Glu | Gln | Leu | Ile | Asn | Gln | Arg | Ile | Glu | Glu |
| | | | | | | | | | | | | | | (m−1) |
| | | | | | | | (c) | | 300 | | | | | |
| TTC | GCT | AGG | AAC | CAA | GCC | ATT | TCT | AGA | TTA | GAA | GGA | CTA | AGC | AAT |
| Phe | Ala | Arg | Asn | Gln | Ala | Ile | Ser | Arg | Leu | Glu | Gly | Leu | Ser | Asn |
| | | | | | | | | | (100) | | | | | |
| CTT | TAT | CAA | ATT | TAC | GCA | GAA | TCT | TTT | AGA | GAG | TGG | GAA | GCA | GAT |
| Leu | Tyr | Gln | Ile | Tyr | Ala | Glu | Ser | Phe | Arg | Glu | Trp | Glu | Ala | Asp |
| CCT | ACT | AAT | CCA | GCA | TTA | AGA | GAA | GAG | ATG | CGT | ATT | CAA | TTC | AAT |
| Pro | Thr | Asn | Pro | Ala | Leu | Arg | Glu | Glu | Met | Arg | Ile | Gln | Phe | Asn |
| | | | | | | | | | | | | | | (135) |

Note: (a) is Bam HI site
(b) is Spe I site
(c) is Xba I site

| | | | | | | | | | | | | | | |
|---|---|---|---|---|---|---|---|---|---|---|---|---|---|---|
| GAC | ATG | AAC | AGT | GCC | CTT | ACA | ACC | GCT | ATT | CCT | CTT | TTT | GCA | GTT |
| Asp | Met | Asn | Ser | Ala | Leu | Thr | Thr | Ala | Ile | Pro | Leu | Phe | Ala | Val |
| | | | | (140) | | | | | | | | | | |
| | | | | | | | | | | | | | | 495 |
| CAA | AAT | TAT | CAA | GTT | CCT | CTT | TTA | TCA | GTA | TAT | GTT | CAA | GCT | GCA |
| Gln | Asn | Tyr | Gln | Val | Pro | Leu | Leu | Ser | Val | Tyr | Val | Gln | Ala | Ala |
| | | | | | | | | | | | | | | (165) |
| | | | | | | | | 523 | | | | | | |
| AAT | TTA | CAT | TTA | TCA | GTT | TTG | AGA | GAT | GTT | TCA | GTG | TTT | GGA | CAA |
| Asn | Leu | His | Leu | Ser | Val | Leu | Arg | Asp | Val | Ser | Val | Phe | Gly | Gln |
| | | | | | | | | | | | | | | (180) |
| | | 549 | | | | | | | | | 577 | | | |
| AGG | TGG | GGA | TTT | GAT | GCC | GCG | ACT | ATC | AAT | AGT | CGT | TAT | AAT | GAT |
| Arg | Trp | Gly | Phe | Asp | Ala | Ala | Thr | Ile | Asn | Ser | Arg | Tyr | Asn | Asp |
| | | | | | | | | | | | | | | (195) |

TABLE A-continued

| | | | | | | | | | | | | | | |
|---|---|---|---|---|---|---|---|---|---|---|---|---|---|---|
| | | | | | | 606 | | | n-348 | | | 624 | | |
| TTA | ACT | AGG | CTT | ATT | GGC | AAC | TAT | ACA | GAT | CAT | GCT | GTA | CGC | TGG |
| Leu | Thr | Arg | Leu | Ile | Gly | Asn | Tyr | Thr | Asp | His | Ala | Val | Arg | Trp |
| | | | | | | | | | (m-116) | | | | | (210) |
| | | | | | | | | | | | | (d) | | 675 |
| TAC | AAT | ACG | GGA | TTA | GAG | CGT | GTA | TGG | GGA | CCG | GAT | TCT | AGA | GAT |
| Tyr | Asn | Thr | Gly | Leu | Glu | Arg | Val | Trp | Gly | Pro | Asp | Ser | Arg | Asp |
| | | | | | | | | | | | | | | (225) |
| TGG | ATA | AGA | TAT | AAT | CAA | TTT | AGA | AGA | GAA | TTA | ACA | CTA | ACT | GTA |
| Trp | Ile | Arg | Tyr | Asn | Gln | Phe | Arg | Arg | Glu | Leu | Thr | Leu | Thr | Val |
| TTA | GAT | ATC | GTT | TCT | CTA | TTT | CCG | AAC | TAT | GAT | AGT | AGA | ACG | TAT |
| Leu | Asp | Ile | Val | Ser | Leu | Phe | Pro | Asn | Tyr | Asp | Ser | Arg | Thr | Tyr |
| | | | | | | | | | | | | | | (255) |
| CCA | ATT | CGA | ACA | GTT | TCC | CAA | TTA | ACA | AGA | GAA | ATT | TAT | ACA | AAC |
| Pro | Ile | Arg | Thr | Val | Ser | Gln | Leu | Thr | Arg | Glu | Ile | Tyr | Thr | Asn |
| CCA | GTA | TTA | GAA | AAT | TTT | GAT | GGT | AGT | TTT | CGA | GGC | TCG | GCT | CAG |
| Pro | Val | Leu | Glu | Asn | Phe | Asp | Gly | Ser | Phe | Arg | Gly | Ser | Ala | Gln |
| GGC | ATA | GAA | GGA | AGT | ATT | AGG | AGT | CCA | CAT | TTG | ATG | GAT | ATA | CTT |
| Gly | Ile | Glu | Gly | Ser | Ile | Arg | Ser | Pro | His | Leu | Met | Asp | Ile | Leu |
| AAC | AGT | ATA | ACC | ATC | TAT | ACG | GAT | GCT | CAT | AGA | GGA | GAA | TAT | TAT |
| Asn | Ser | Ile | Thr | Ile | Tyr | Thr | Asp | Ala | His | Arg | Gly | Glu | Tyr | Tyr |
| TGG | TCA | GGG | CAT | CAA | ATA | ATG | GCT | TCT | CCT | GTA | GGG | TTT | TCG | GGG |
| Trp | Ser | Gly | His | Gln | Ile | Met | Ala | Ser | Pro | Val | Gly | Phe | Ser | Gly |

Note: (d) is Xba I site

| | | | | | | | | | | | | | | |
|---|---|---|---|---|---|---|---|---|---|---|---|---|---|---|
| CCA | GAA | TTC | ACT | TTT | CCG | CTA | TAT | GGA | ACT | ATG | GGA | AAT | GCA | GCT |
| Pro | Glu | Phe | Thr | Phe | Pro | Leu | Tyr | Gly | Thr | Met | Gly | Asn | Ala | Ala |
| CCA | CAA | CAA | CGT | ATT | GTT | GCT | CAA | CTA | GGT | CAG | GGC | GTG | TAT | AGA |
| Pro | Gln | Gln | Arg | Ile | Val | Ala | Gln | Leu | Gly | Gln | Gly | Val | Tyr | Arg |
| ACA | TTA | TCG | TCC | ACT | TTA | TAT | AGA | AGA | CCT | TTT | AAT | ATA | GGG | ATA |
| Thr | Leu | Ser | Ser | Thr | Leu | Tyr | Arg | Arg | Pro | Phe | Asn | Ile | Gly | Ile |
| AAT | AAT | CAA | CAA | CTA | TCT | GTT | CTT | GAC | GGG | ACA | GAA | TTT | GCT | TAT |
| Asn | Asn | Gln | Gln | Leu | Ser | Val | Leu | Asp | Gly | Thr | Glu | Phe | Ala | Tyr |
| GGA | ACC | TCC | TCA | AAT | TTG | CCA | TCC | GCT | GTA | TAC | AGA | AAA | AGC | GGA |
| Gly | Thr | Ser | Ser | Asn | Leu | Pro | Ser | Ala | Val | Tyr | Arg | Lys | Ser | Gly |
| ACG | GTA | GAT | TCG | CTG | GAT | GAA | ATA | CCG | CCA | CAG | AAT | AAC | AGC | GTG |
| Thr | Val | Asp | Ser | Leu | Asp | Glu | Ile | Pro | Pro | Gln | Asn | Asn | Asn | Val |
| CCA | CCT | AGG | CAA | GGA | TTT | AGT | CAT | CGA | TTA | AGC | CAT | GTT | TCA | ATG |
| Pro | Pro | Arg | Gln | Gly | Phe | Ser | His | Arg | Leu | Ser | His | Val | Ser | Met |
| | | | | | | | | | | | | | | 1350 |
| TTG | CGT | TCA | GGC | TTT | AGT | AAT | AGT | AGT | GTA | AGT | ATA | ATA | AGA | GCT |
| Phe | Arg | Ser | Gly | Phe | Ser | Asn | Ser | Ser | Val | Ser | Ile | Ile | Arg | Ala |
| | | | | | | | | | | | | | | (450) |
| CCT | ATG | TTC | TCT | TGG | ATA | CAT | CGT | AGT | GCT | GAA | TTT | AAT | AAT | ATA |
| Pro | Met | Phe | Ser | Trp | Ile | His | Arg | Ser | Ala | Glu | Phe | Asn | Asn | Ile |
| ATT | CCT | TCA | TCA | CAA | ATT | ACA | CAA | ATA | CCT | TTA | ACA | AAA | TCT | ACT |
| Ile | Pro | Ser | Ser | Gln | Ile | Thr | Gln | Ile | Pro | Leu | Thr | Lys | Ser | Thr |
| AAT | CTT | GGC | TCT | GGA | ACT | TCT | GTC | GTT | AAA | GGA | CCA | GGA | TTT | ACA |
| Asn | Leu | Gly | Ser | Gly | Thr | Ser | Val | Val | Lys | Gly | Pro | Gly | Phe | Thr |
| GGA | GGA | GAT | ATT | CTT | CGA | AGA | ACT | TCA | CCT | GGC | CAG | ATT | TCA | ACC |
| Gly | Gly | Asp | Ile | Leu | Arg | Arg | Thr | Ser | Pro | Gly | Gln | Ile | Ser | Thr |
| TTA | AGA | GTA | AAT | ATT | ACT | GCA | CCA | TTA | TCA | CAA | AGA | TAT | CGG | GTA |
| Leu | Arg | Val | Asn | Ile | Thr | Ala | Pro | Leu | Ser | Gln | Arg | Tyr | Arg | Val |
| AGA | ATT | CGC | TAC | GCT | TCT | ACC | ACA | AAT | TTA | CAA | TTC | CAT | ACA | TCA |
| Arg | Ile | Arg | Tyr | Ala | Ser | Thr | Thr | Asn | Leu | Gln | Phe | His | Thr | Ser |
| ATT | GAC | GGA | AGA | CCT | ATT | AAT | CAG | GGG | AAT | TTT | TCA | GCA | ACT | ATG |
| Ile | Asp | Gly | Arg | Pro | Ile | Asn | Gln | Gly | Asn | Phe | Ser | Ala | Thr | Met |

TABLE A-continued

| | | | | | | | | | | | | | | |
|---|---|---|---|---|---|---|---|---|---|---|---|---|---|---|
| AGT | AGT | GGG | AGT | AAT | TTA | CAG | TCC | GGA | AGC | TTT | AGG | ACT | GTA | GGT |
| Ser | Ser | Gly | Ser | Asn | Leu | Gln | Ser | Gly | Ser | Phe | Arg | Thr | Val | Gly |
| TTT | ACT | ACT | CCG | TTT | AAC | TTT | TCA | AAT | GGA | TCA | AGT | GTA | TTT | ACG |
| Phe | Thr | Thr | Pro | Phe | Asn | Phe | Ser | Asn | Gly | Ser | Ser | Val | Phe | Thr |
| TTA | AGT | GCT | CAT | GTC | TTC | AAT | TCA | GGC | AAT | GAA | GTT | TAT | ATA | GAT |
| Leu | Ser | Ala | His | Val | Phe | Asn | Ser | Gly | Asn | Glu | Val | Tyr | Ile | Asp |
| CGA | ATT | GAA | TTT | GTT | CCG | GCA | GAA | GTA | ACC | TTT | GAG | GCA | GAA | TAT |
| Arg | Ile | Glu | Phe | Val | Pro | Ala | Glu | Val | Thr | Phe | Glu | Ala | Glu | Tyr |
| | | | | | | | | | (610) | | | | | |
| GAT | TTA | GAA | AGA | GCA | CAA | AAG | GCG | GTG | AAT | GAG | CTG | TTT | ACT | TCT |
| Asp | Leu | Glu | Arg | Ala | Gln | Lys | Ala | Val | Asn | Glu | Leu | Phe | Thr | Ser |
| TCC | AAT | CAA | ATC | GGG | TTA | AAA | ACA | GAT | GTG | ACG | GAT | TAT | CAT | ATT |
| Ser | Asn | Gln | Ile | Gly | Leu | Lys | Thr | Asp | Val | Thr | Asp | Tyr | His | Ile |
| GAT | CAA | GTA | TCC | AAT | TTA | GTT | GAG | TGT | TTA | TCT | GAT | GAA | TTT | TGT |
| Asp | Gln | Val | Ser | Asn | Leu | Val | Glu | Cys | Leu | Ser | Asp | Glu | Phe | Cys |
| CTG | GAT | GAA | AAA | AAA | GAA | TTG | TCC | GAG | AAA | GTC | AAA | CAT | GCG | AAG |
| Leu | Asp | Glu | Lys | Lys | Glu | Leu | Ser | Glu | Lys | Val | Lys | His | Ala | Lys |
| CGA | CTT | AGT | GAT | GAG | CGG | AAT | TTA | CTT | CAA | GAT | CCA | AAC | TTT | AGA |
| Arg | Leu | Ser | Asp | Glu | Arg | Asn | Leu | Leu | Gln | Asp | Pro | Asn | Phe | Arg |
| GGG | ATC | AAT | AGA | CAA | CTA | GAC | CGT | GGC | TGG | AGA | GGA | AGT | ACG | GAT |
| Gly | Ile | Asn | Arg | Gln | Leu | Asp | Arg | Gly | Trp | Arg | Gly | Ser | Thr | Asp |
| ATT | ACC | ATC | CAA | GGA | GGC | GAT | GAC | GTA | TTC | AAA | GAG | AAT | TAC | GTT |
| Ile | Thr | Ile | Gln | Gly | Gly | Asp | Asp | Val | Phe | Lys | Glu | Asn | Tyr | Val |
| | | | (d) | | | | | | | | | | | |
| ACG | CTA | TTG | GGT | ACC | TTT | GAT | GAG | TGC | TAT | CCA | ACG | TAT | TTA | TAT |
| Thr | Leu | Leu | Gly | Thr | Phe | Asp | Glu | Cys | Tyr | Pro | Thr | Tyr | Leu | Tyr |
| | | (723) | | | | | | | | | | | | |
| | | | | | | | | | | | | | | 2250 |
| CAA | AAA | ATA | GAT | GAG | TCG | AAA | TTA | AAA | GCC | TAT | ACC | CGT | TAC | CAA |
| Gln | Lys | Ile | Asp | Glu | Ser | Lys | Leu | Lys | Ala | Tyr | Thr | Arg | Tyr | Gln |
| | | | | | | | | | | | | | | (750) |
| TTA | AGA | GGG | TAT | ATC | GAA | GAT | AGT | CAA | GAC | TTA | GGA | ATC | TAT | TTA |
| Leu | Arg | Gly | Tyr | Ile | Glu | Asp | Ser | Gln | Asp | Leu | Glu | Ile | Tyr | Leu |
| ATT | CGC | TAC | AAT | GCC | AAA | CAC | GAA | ACA | GTA | AAT | GTG | CCA | GGT | ACG |
| Ile | Arg | Tyr | Asn | Ala | Lys | His | Glu | Thr | Val | Asn | Val | Pro | Gly | Thr |
| GGT | TCC | TTA | TGG | CCG | CTT | TCA | GCC | CCA | AGT | CCA | ATC | GGA | AAA | TGT |
| Gly | Ser | Leu | Trp | Pro | Leu | Ser | Ala | Pro | Ser | Pro | Ile | Gly | Lys | Cys |

Note: (d) is Kpn I site

| | | | | | | | | | | | | | | |
|---|---|---|---|---|---|---|---|---|---|---|---|---|---|---|
| GGA | GAA | CCG | AAT | CGA | TGC | GCA | CCA | CAA | CTT | GAA | TGG | AAT | CCA | GAT |
| Gly | Glu | Pro | Asn | Arg | Cys | Ala | Pro | Gln | Leu | Glu | Trp | Asn | Pro | Asp |
| CTA | GAT | TGT | TCC | TGC | AGA | GAC | GGA | GAA | AAA | TGT | GCC | CAT | CAT | TCC |
| Leu | Asp | Cys | Ser | Cys | Arg | Asp | Gly | Glu | Lys | Cys | Ala | His | His | Ser |
| CAT | CAT | TTC | TCC | TTG | GAC | ATT | GAT | GTT | GGA | TGT | ACA | GAC | TTA | AAT |
| His | His | Phe | Ser | Leu | Asp | Ile | Asp | Val | Gly | Cys | Thr | Asp | Leu | Asn |
| | | | | | | | | | | | | | | (840) |
| GAG | GAC | TTA | GGT | GTA | TGG | GTG | ATA | TTC | AAG | ATT | AAG | ACG | CAA | GAT |
| Glu | Asp | Leu | Gly | Val | Trp | Val | Ile | Phe | Lys | Ile | Lys | Thr | Gln | Asp |
| GGC | CAT | GCA | AGA | CTA | GGA | AAT | CTA | GAA | TTT | CTC | GAA | GAG | AAA | CCA |
| Gly | His | Ala | Arg | Leu | Gly | Asn | Leu | Glu | Phe | Leu | Glu | Glu | Lys | Pro |
| TTA | GTA | GGA | GAA | GCA | CTA | GCT | CGT | GTG | AAA | AGA | GCG | GAG | AAA | AAA |
| Leu | Val | Gly | Glu | Ala | Leu | Ala | Arg | Val | Lys | Arg | Ala | Glu | Lys | Lys |
| | | | | | | | | | | | | | | 2700 |
| TGG | AGA | GAC | AAA | CGT | GAA | AAA | TTG | GAA | TGG | GAA | ACA | AAT | ATT | GTT |
| Trp | Arg | Asp | Lys | Arg | Glu | Lys | Leu | Glu | Trp | Glu | Thr | Asn | Ile | Val |
| | | | | | | | | | | | | | | (900) |
| TAT | AAA | GAG | GCA | AAA | GAA | TCT | GTA | GAT | GCT | TTA | TTT | GTA | AAC | TCT |
| Tyr | Lys | Glu | Ala | Lys | Glu | Ser | Val | Asp | Ala | Leu | Phe | Val | Asn | Ser |

TABLE A-continued

| | | | | | | | | | | | | | | |
|---|---|---|---|---|---|---|---|---|---|---|---|---|---|---|
| CAA | TAT | GAT | AGA | TTA | CAA | GCG | GAT | ACC | AAC | ATC | GCG | ATG | ATT | CAT |
| Gln | Tyr | Asp | Arg | Leu | Gln | Ala | Asp | Thr | Asn | Ile | Ala | Met | Ile | His |
| GCG | GCA | GAT | AAA | CGC | GTT | CAT | AGC | ATT | CGA | GAA | GCT | TAT | CTG | CCT |
| Ala | Ala | Asp | Lys | Arg | Val | His | Ser | Ile | Arg | Glu | Ala | Tyr | Leu | Pro |
| GAG | CTG | TCT | GTG | ATT | CCG | GGT | GTC | AAT | GCG | GCT | ATT | TTT | GAA | GAA |
| Glu | Leu | Ser | Val | Ile | Pro | Gly | Val | Asn | Ala | Ala | Ile | Phe | Glu | Glu |
| TTA | GAA | GGG | CGT | ATT | TTC | ACT | GCA | TTC | TCC | CTA | TAT | GAT | GCG | AGA |
| Leu | Glu | Gly | Arg | Ile | Phe | Thr | Ala | Phe | Ser | Leu | Tyr | Asp | Ala | Arg |
| AAT | GTC | ATT | AAA | AAT | GGT | GAT | TTT | AAT | AAT | GGC | TTA | TCC | TGC | TGG |
| Asn | Val | Ile | Lys | Asn | Gly | Asp | Phe | Asn | Asn | Gly | Leu | Ser | Cys | Trp |
| AAC | GTG | AAA | GGG | CAT | GTA | GAT | GTA | GAA | GAA | CAA | AAC | AAC | CAC | CGT |
| Asn | Val | Lys | Gly | His | Val | Asp | Val | Glu | Glu | Gln | Asn | Asn | His | Arg |
| TCG | GTC | CTT | GTT | GTT | CCG | GAA | TGG | GAA | GCA | GAA | GTG | TCA | CAA | GAA |
| Ser | Val | Leu | Val | Val | Pro | Glu | Trp | Glu | Ala | Glu | Val | Ser | Gln | Glu |
| GTT | CGT | GTC | TGT | CCG | GGT | CGT | GGC | TAT | ATC | CTT | CGT | GTC | ACA | GCG |
| Val | Arg | Val | Cys | Pro | Gly | Arg | Gly | Tyr | Ile | Leu | Arg | Val | Thr | Ala |
| TAC | AAG | GAG | GGA | TAT | GGA | GAA | GGT | TGC | GTA | ACC | ATT | CAT | GAG | ATC |
| Tyr | Lys | Glu | Gly | Tyr | Gly | Glu | Gly | Cys | Val | Thr | Ile | His | Glu | Ile |
| | | | | | | | | | | | | | | (1050) |
| GAG | AAC | AAT | ACA | GAC | GAA | CTG | AAG | TTT | AGC | AAC | TGT | GTA | GGA | GAG |
| Glu | Asn | Asn | Thr | Asp | Glu | Leu | Lys | Phe | Ser | Asn | Cys | Val | Glu | Glu |
| | | | | | | | | | | | | | | 3240 |
| GAA | GTA | TAT | CCA | AAC | AAC | ACG | GTA | ACG | TGT | AAT | GAT | TAT | ACT | GCG |
| Glu | Val | Tyr | Pro | Asn | Asn | Thr | Val | Thr | Cys | Asn | Asp | Tyr | Thr | Ala |
| | | | | | | | | | | | | | | (1080) |
| ACT | CAA | GAA | GAA | TAT | GAG | GGT | ACG | TAC | ACT | TCT | CGT | AAT | CGA | GGA |
| Thr | Gln | Glu | Glu | Tyr | Glu | Gly | Thr | Tyr | Thr | Ser | Arg | Asn | Arg | Gly |
| TAT | GAC | GGA | GCT | TAT | GAA | AGC | AAT | TCT | TCT | GTA | CCA | GCT | GAT | TAT |
| Tyr | Asp | Gly | Ala | Tyr | Glu | Ser | Asn | Ser | Ser | Val | Pro | Ala | Asp | Tyr |
| GCA | TCA | GCC | TAT | GAA | GAA | AAA | GCA | TAT | ACA | GAT | GGA | CGA | AGA | GAC |
| Ala | Ser | Ala | Tyr | Glu | Glu | Lys | Ala | Tyr | Thr | Asp | Gly | Arg | Arg | Asp |
| AAT | CCT | TGT | GAA | TCT | AAC | AGA | GGA | TAT | GGG | GAT | TAC | ACA | CCA | CTA |
| Asn | Pro | Cys | Glu | Ser | Asn | Arg | Gly | Tyr | Gly | Asp | Tyr | Thr | Pro | Leu |
| CCA | GCT | GGC | TAT | GTG | ACA | AAA | GAA | TTA | GAG | TAC | TTC | CCA | GAA | ACC |
| Pro | Ala | Gly | Tyr | Val | Thr | Lys | Glu | Leu | Glu | Tyr | Phe | Pro | Glu | Thr |
| GAT | AAG | GTA | TGG | ATT | GAG | ATC | GGA | GAA | ACG | GAA | GGA | ACA | TTC | ATT |
| Asp | Lys | Val | Trp | Ile | Glu | Ile | Gly | Glu | Thr | Glu | Gly | Thr | Phe | Ile |
| | | | | | | | | | | | | | | (1170) |
| GTG | GAT | AGC | GTG | GAA | TTA | CTC | CTT | ATG | GAG | GAA | TAG | | | |
| Val | Asp | Ser | Val | Glu | Leu | Leu | Leu | Met | Glu | Glu | * * * | | | |
| | | | | | | | | | | (1181) | | | | |

What is claimed is:

1. A process for transforming *Bacillus thuringiensis* (*B. thuringiensis*) with exogenous DNA comprising establishing a hypertonic aqueous transformation medium containing said host cells and said exogenous DNA to be transformed into said cells, subjecting said transformation medium containing said host cells and said exogenous DNA to a voltage pulsed current of about 1500 to 3000 volts to effect transformation of said host cells by said exogenous DNA, and incubating the thus transformed host cells in a hypertonic aqueous incubation medium for a time sufficient to obtain transformed host cells.

2. The process of claim 1 in which the host cells prior to incorporation into said hypertonic aqueous transformation medium are grown to a cell density OD600 of from 0.55 to 0.8.

3. The process of claim 2 in which the host cells are grown to a cell density of 0.6 to 0.75.

4. The process of claim 2 in which the host cells are transformed with current pulsed at a voltage of 2300 to 2600 volts.

5. The process of claim 4 in which the host cells prior to incorporation into said hypertonic aqueous transformation medium are grown in a hypertonic aqueous medium.

6. The process of claim 2 in which the host cells prior to incorporation into said hypertonic aqueous transformation medium are grown in a hypertonic aqueous medium.

7. The process of claim 1 in which the host cells prior to incorporation into said hypertonic aqueous medium are grown in a hypertonic aqueous transformation medium.

8. The process of claim 7 in which the hypertonic growth medium contains 0.35M to 0.55M of sucrose as a means for inducing its hypertonic status.

9. The process of claim 8 in which the hypertonic growth media contains lysozyme in an amount less than that which would render the cells protoplastic.

10. The process of claim 9 in which the lysozyme concentration is from 20 to 300 micrograms per ml of the hypertonic aqueous mediua.

11. The process of claim 1 in which the hypertonic transformation medium and hypertonic recovery medium contain 0.35M to 0.55M of sucrose as means for inducing their hypertonic status.

12. The process of claim 1 in which the DNA is plasmid DNA comprising a DNA sequence operable in *B. thuringiensis* and encoding an endotoxin protein, an origin of replication in *B. thuringiensis* and a DNA gene sequence operable in *B. thuringiensis* and encoding antibiotic resistance.

13. The process of claim 1 in which the host cells are *B. thuringiensis kurstaki* cells.

14. The process of claim 1 in which the host cells are *B. thuringiensis tenebrionis* cells.

15. The process of claim 1 in which the host cells are *B. thuringiensis aisawai* cells.

16. A process for transforming *Bacillus thuringiensis* with exogenous DNA from *B. thuringiensis* donor cells comprising establishing a hypertonic aqueous transformation medium containing said host cells and said exogenous DNA to be transformed into said cells, subjecting said transformation medium containing said host cells and said exogenous DNA to a voltage pulsed current between 2200 to 3000 volts to effect transformation of said host cells by said exogenous DNA, and incubating the thus transformed host cells hypertonic aqueous incubation medium for a time sufficient to obtain transformed host cells.

17. The process of claim 16 wherein the exogenous DNA is from a *B. thuringiensis* donor cell of the same subspecies as the host cell.

18. The process of claim 16 wherein the exogenous DNA is from a *B. thuringiensis* donor cell of a different subspecies as the host cell.

19. The process according to claim 16 wherein the hypertonic aqueous transformation medium further comprises lysozyme in an amount not more than 500 micrograms per ml of hypertonic medium.

20. The process of claim 16 wherein the host cells are *B. thuringiensis kurstaki* cells.

* * * * *